United States Patent [19]

Hansen, Jr. et al.

[11] Patent Number: 4,603,121

[45] Date of Patent: * Jul. 29, 1986

[54] ENKEPHALIN ANALOGS

[75] Inventors: Donald W. Hansen, Jr., Chicago; David A. Jones, Jr., Evanston; Robert H. Mazur, Chicago; James M. Schlatter, Glenview, all of Ill.

[73] Assignee: G.D. Searle & Co., Skokie, Ill.

[*] Notice: The portion of the term of this patent subsequent to Jan. 22, 2002 has been disclaimed.

[21] Appl. No.: 650,145

[22] Filed: Sep. 14, 1984

Related U.S. Application Data

[63] Continuation-in-part of Ser. No. 539,458, Oct. 6, 1983, Pat. No. 4,495,178.

[51] Int. Cl.$^4$ ............... A61K 37/24; C07K 7/12
[52] U.S. Cl. ............... 514/18; 514/809; 530/302
[58] Field of Search ............... 260/112.5 E; 514/18, 514/809

[56] References Cited

U.S. PATENT DOCUMENTS 4,407,746  10/1983  Mazur et al. ............... 260/112.5 E
4,495,178  1/1985  Hansen, Jr. et al. ............... 260/112.5 R

*Primary Examiner*—Delbert R. Phillips
*Attorney, Agent, or Firm*—Stuart L. Melton; John J. McDonnell

[57] ABSTRACT

The invention relates to novel enkephalin analogs of the formula:

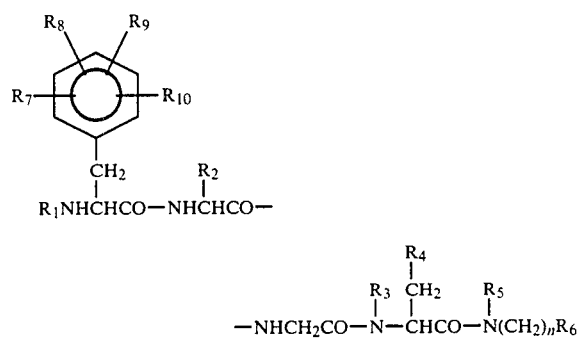

which are useful as analgesic agents.

15 Claims, No Drawings

ENKEPHALIN ANALOGS

BACKGROUND OF THE INVENTION

This application is a continuation-in-part application of co-pending application Ser. No. 539,458 filed Oct. 6, 1983, now U.S. Pat. No. 4,495,178.

The present invention relates to novel enkephalin derivatives. In particular, it provides novel enkephalin derivatives of Formula I which are useful as analgesic agents.

In 1975, a pentapeptide, methionine enkephalin, was reported by Hughes et al., *Nature,* 258, 577 (1975). This peptide is found in many areas of the brain where it appears to act as a neurotransmitter or neuromodulator in a central pain-suppressant system. The natural peptide binds stereospecifically to partially purified brain opiate receptor sites, see for example, Bradberry et al., *Nature,* 260, 793 (1976). The natural peptide is also highly active in bioassays for opiate activity but exhibits only weak, fleeting analgesic activity when injected directly into the brain of the rat, see for example, Belluzi et al., *Nature,* 260, 625 (1976)

In order to overcome the lack of in vivo activity, a number of investigators have made numerous modifications in the methionine enkephalin structure, such as substituting the glycine in the 2-position with a D-amino acid, N-methylation of the L-tyrosine, substituting the 4-phenylalanine with, for example, methyl or halo, modifying the C-terminus, etc., to produce enkephalin derivatives of varying properties and potencies. The present invention provides new enkephalin derivatives which approach the potency of morphine as analgesic agents by both oral and parenteral routes of administration.

INFORMATION DISCLOSURE

U.S. Pat. No. 4,316,892 relates to certain derivatives of methionine enkaphalin derivatives useful as analgesic agents.

SUMMARY OF THE INVENTION

The present invention particularly provides enkephalin derivatives according to Formula I.

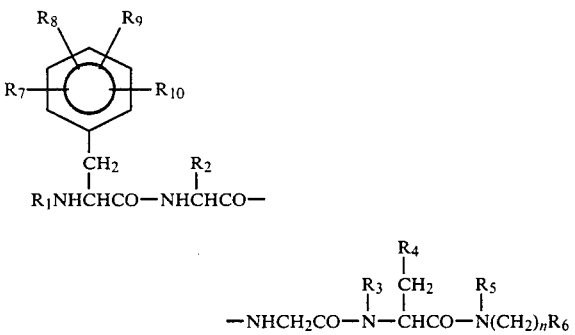

wherein $R_1$ is:
(a) hydrogen; or
(b) alkyl of 1 to 6 carbon atoms, inclusive;
wherein $R_2$ is:
(a) alkyl of 1 to 6 carbon atoms, inclusive; or
(b)

$$-CH_2CH_2SCH_3;$$
$$\quad\quad\quad\quad\;\; |$$
$$\quad\quad\quad\quad\;\; O_m$$

m being either zero, 1 or 2;
wherein $R_3$ is:
(a) hydrogen; or
(b) alkyl of 1 or 2 carbon atoms; inclusive;
wherein $R_4$ is:
(a) phenyl, optionally substituted by alkyl of 1 to 6 carbon atoms, inclusive; or
(b) cyclohexyl, optionally substituted by alkyl of 1 to 6 carbon atoms, inclusive;
wherein $R_5$ is:
(a) hydrogen; or
(b) alkyl of 1 to 6 carbon atoms, inclusive;
wherein $R_6$ is:
(a) carboxy;
(b) alkoxycarbonyl of 2 to 7 carbon atoms, inclusive;
(c) $CONH_2$;
(d) N,N-dialkylcarbamoyl of 3 to 7 carbon atoms, inclusive;
(e) hydroxy; or
(f) alkanoyloxy of 2 to 7 carbon atoms, inclusive;
wherein $R_7$, $R_8$, and $R_9$ are H or alkyl of 1 to 6 carbon atoms, and may be the same or different;
wherein $R_{10}$ is:
(a) hydrogen;
(b) hydroxy; or
(c) alkoxycarbonyloxy wherein the alkoxy portion is from 1 to 6 carbon atoms, inclusive;
wherein n is an integer of from 3 to 10 inclusive and the pharmocologically acceptable acid addition salts thereof.

Example of alkoxy of one to six carbon atoms, inclusive, are methoxy, ethoxy, propoxy, butoxy, pentoxy, hexoxy, and the isomeric forms thereof.

Examples of alkyl of one to six carbon atoms inclusive, are methyl, ethyl, propyl, butyl, pentyl, and hexyl and the isomeric forms thereof.

The analgesic activity for the compounds of the present invention was established in the hot-plate assay and mouse PBQ-writhing assay, and the analgesic activity of the representative compounds was compared with that of morphine.

Hot-plate assay. Male CRL: COBX CD-1 (1CR) BR mice weighing 20 to 30 grams are used. Two groups of 14 mice are brought into the experiment room approximately one-half hour prior to testing. The mice are placed individually in a restraining cylinder placed on a hot plate with temperature controlled by a proportional temperature controller at 55 degrees plus or minus 0.5 degrees centigrade. The reaction time of each mouse to lick a foot or jump is measured 3 times at 20 minute intervals. Mice not responding within 15 seconds are discarded. Ten mice are given a dose of the test drug and ten are given 0.9 percent saline, each containing approximately 0.09 ml of a 50/50 mixture of propylene glycol and polysorbate 80, intraveneously 20 minutes after the last reaction time measurement. The animals are tested as before 10, 30, and 60 seconds after this injection. Mice not responding within 30 seconds are removed from the hot plate and given a response time of 30 seconds. Analgesia is considered to be demonstrated in the mouse if its post-drug reaction time is greater than that of the control mean plus two standard deviations. The number of animals showing analgesia in the drug group is compared with that same value for the control group by means of Fisher's exact probability test. The $ED_{50}$ is then calculated. N. B. Eddy et al. *Synthetic Analgesics*, National Institute of Arthritis and Metabolic Diseases, National Institute of Health Bethesda, Maryland, pages 385-393, 1952, and S. Siegal: *Non-parametrics Statistics for the Behavioral Sciences*, New York: McGraw Hill Book Company, 1956.

PBQ-Writhing assay. Groups of 10 male mice weighing 20 to 35 grams are used for each dose and for the vehicle control. Writhing is induced 30 or 60 minutes following drug or drug vehicle administration by the intraperitoneal injection of a 0.025 percent solution of PBQ and .5 percent ethanol. The number of separate writhing motions occurring in a ten minute period starting 5 minutes following the PBQ challenge is counted for each mouse. A positive antinociceptive affect is assured when an individual animals' writhing frequency is less than or equal to 50 percent of the vehicle control group median frequency. $ED_{50}$ values based on the number of positive responders per dose group is determined using the method of Litchfield and Wilcoxon. M. R. Fennessy et al. *The Assessment of and Problems Involved in the Experimental Evaluation of Narcotic Analgesics.* In *Methods in Narcotics Research*, Marcel Dekker, Inc., New York, 1975. H. Bomberg et al. *Use of Writhing Test for Evaluating Analgesic Activity of Narcotic Analgesics*, Proc. Soc. Ext. Biol. Med. 118: 763-766, 1965. These tests show that the novel compounds are useful as analgesic agents in the dosage ranges about 0.1 to 100 milligrams per kilogram.

By virtue of the analgesic activity, the compounds of Formula I are useful in treating symptoms requiring an analgesic in humans and animals. A physician or veterinarian of ordinary skill could readily determine a subject who is exhibiting such symptoms. Regardless of the route of administration selected, the compounds of the present invention are formulated into pharmaceutically acceptable dosage forms by conventional methods known to the pharmaceutical art. The compounds can be administered in such oral dosage forms as tablets, capsules, pills, powders, granules, suspensions, or solutions. They may also be administered rectally or vaginally, in such forms as suppositories or bougies. They may also introduced in the form of eyedrops, intraperitoneally, subcutaneously or intramuscularly, using forms known to the pharmaceutical art. In general the preferred form of administration is oral.

An effective but nontoxic quantity of the compound is employed in treatment. The dosage regimen for preventing or treating symptoms by the compounds of this invention is selected in accordance with a variety of factors including the type, age, weight, sex, and medical condition of the mammal, the severity of the symptoms, the route of administration of the particular compound employed. An ordinary skilled physician or veterinarian will readily determine and prescribe the effective amount based on the route of administration of the analgesic agent to prevent or arrest the progress of the condition. In so proceeding, the physician or veterinarian could employ relatively low dosages at first, subsequently increasing the dose until a maximum response is obtained.

The compounds of Formula I can also be administered as pharmacologically acceptable acid addition salts such as the hydrochloride, hydrobromide, hydroiodide, sulfate, phosphate, acetate, propionate, lactate, maleate, malate, succinate, tartrate and the like. Additionally, the compounds of this invention may be administered in a suitable hydrated form.

The compounds of this invention may be prepared by any number of methods known to those skilled in the art. For example, the particular sequence of reactions by which the individual amino acids are joined to form the compounds of Formula I is generally not of critical importance, being chosen principally for convenience or for maximum yields. Moreover, the choice of activating reagents and conditions for joining amino acids or small peptides is not limited to those specifically described herein. Peptide intermediates and products of this invention are typically purified by crystallization, where possible, or by column chromatography. Furthermore, where racemic amino acid starting materials are employed, intermediates and products may be separated during column chromatography into diastereomers. For example, reaction of racemic-t butoxycarbonyl-2,6-dimethyl(D,L) tyrosine with a peptide intermediate results in mixtures of diastereomeric products. Based upon thin layer chromatography results, these diastereomers are comprised of a slow moving isomer (S) and a faster moving isomer (F). In describing these isomers herein, the assumption is made that the slow moving diastereomer (S) corresponds to the L-isomer and the fast moving diasteriomer (F) corresponds to the D-isomer form of the tyrosyl starting material.

The accompanying Charts are used to illustrate one of the possible methods used to prepare the compounds of this invention.

Chart A illustrates a general method for forming dipeptide intermediates useful in the synthesis of compounds of Formula I. Partially blocked amino acids of Formula XI, in which B represents common N-protecting groups such as t-butoxycarbonyl, may be activated by any of several methods known to those skilled in the art. The generally preferred method includes forming a mixed anhydride by reaction with an alkyl chlorocarbonate in an unreactive solvent containing a tertiary amine. Preferred conditions include cooling a mixture of the appropriate compound of Formula XI in cold (ca. $-30$ to $-40°$) dimethylformamide or dichloromethane containing N-methylmorpholine, followed by addition of isobutyl chloroformate. Once the mixed anhydride of Formula XII ($X=OCOOCH_2CH(CH_3)_2$) has formed, the appropriate amine of Formula XIII is added and the reaction allowed to proceed at room temperature, giving the fully blocked intermediates of Formula XIV.

Especially where the amine of Formula XIII is N-substituted (i.e., where $R_5$ is not hydrogen), an alternative method of activation involving carbodiimides may be more appropriate. For this method, compounds of Formulas XI and XIII are stirred together in an unreactive solvent to which is then added the carbodiimide. Preferred conditions include reaction in dichloromethane using dicyclohexylcarbodiimide. The isolated intermediates, Formula XIV, are exactly the same as those formed by the mixed anhydride method.

Using methods appropriate for the particular protecting groups B, compounds of Formula XIV may readily be deprotected to give compounds XV. Where the t-butoxycarbonyl protecting group is employed, for example, preferred deblocking conditions include acid solvolysis in hydrogen chloride/dioxane. Typically, the resultant hydrochloride salts may be used in subsequent reactions without first isolating the free amine.

Chart B illustrates one method for extending the peptide chain to form intermediates of Formula XXVII.

Using methods described above (see also Chart A), fully protected intermediates of Formula XXIV are formed fron N-protected amino acids, Formula XXI, and omega-amino esters, Formula XXIII. Hydrolysis of these intermediates, Formula XXIV, affords the analogous acids of Formula XXV. Preferred hydrolysis conditions include approximately one molar sodium hydroxide in aqueous methanol, followed by neutralization with sodium bisulfate. Using the methods described above, compounds of Formula XXV are activated and then coupled with intermediates of Formula XV to form protected peptides of Formula XXVI. As described above (see Chart A), removal of the protecting groups B affords amino compounds of Formula XXVII.

Chart C illustrates one method for completing the extension of the peptide chains. As described before (see Charts A and B), suitably protected aromatic amino acids of Formula XXXI are activated, for example by using mixed anhydride or carbodiimide methods, and allowed to react with intermediates of Formula XXVII. Appropriate removal of protecting groups from compounds XXXII affords compounds of this invention, Formula I.

Chart D illustrates one method for preparing sulfoxide or sulfone members of this invention, Formula XLII (i.e., Formula I where $R=CH_2CH_2S(O)CH_3$ or $R=CH_2CH_2SO_2-CH_3$, respectively), which for practical reasons are generally prepared after the methionine-containing peptides of Formula XLI have been fully formed using methods described above. Preferred oxidizing conditions include hydrogen peroxide in aqueous methanol—at room temperature, sulfoxides are the predominant or sole oxidation product, whereas at elevated temperatures (e.g., refluxing solvent), sulfones are formed.

The invention will appear more fully from the examples which follow. These examples are given by way of illustration only, and are not to be construed as limiting the invention either in spirit or in scope, as many modifications both in materials and in methods will be apparent from this disclosure to those skilled in the art.

DESCRIPTION OF THE PREFERRED EMBODIMENTS

EXAMPLE 1 t-butoxycarbonyl-N-(5-methoxy-5-oxopentyl)-L-phenylalaninamide

To a cold (ca $-30°$), stirred solution of 26.5 g (0.1 mole) of t-butoxycarbonylphenylalanine (BOC-Phe) and 11.2 g (0.1 mole) of N-methylmorpholine in 150 ml of dimethylformamide (DMF) was added dropwise 13.2 ml (0.1 mole) of isobutylchloroformate. After warming and then holding the temperature at ca. $-15°$ for about ten minutes, the solution was recooled to ca. $-39°$. To the cold mixture was added additional N-methylmorpholine (12.3 ml, ca. 0.11 mole), followed by 18.5 g (0.11 mole) of methyl 5-aminopentanoate hydrochloride. The mixture was allowed to warm to room temperature and to stand overnight. Solvent and other volatiles were removed by concentration in vacuo. The residue was triturated with ethyl acetate, which was then washed successively with water, 0.5 M potassium bisulfate, water, and again with 0.5 M potassium bisulfate, and then dried over magnesium sulfate, filtered, and concentrated to a white solid. After collection, the white solid was washed thoroughly with Skellysolve B to give 36.4 g of the title compound, m.p. $98°-100°$. Recrystallization from ethyl acetate/Skellysolve B afforded analytically pure crystals.

Analysis. Calcd. For $C_{20}H_{30}N_2O_5$: C, 63.47; H, 7.99; N, 7.40. Found: C, 63.32; H, 8.03; N, 7.24.

EXAMPLE 2 t-butoxycarbonyl-N-(6-methoxy-6-oxohexyl)-L-phenylalaninamide

The title compound was prepared by the method of Example 1 using methyl 6-aminohexanoate hydrochloride and was used in subsequent reactions without further purification.

EXAMPLE 3

N-(6-methoxy-6-oxohexyl)-L-phenylalaninamide monohydrochloride

To a solution of the title compound of Example 2 (43.1 g, 0.11 mole) in 100 ml of dioxane was added 100 ml of 6 M hydrogen chloride/dioxane. After about 30 min. the solution was concentrated in vacuo to dryness and the residue triturated thoroughly with diethyl ether. The solid was collected and washed well with diethyl ether, giving 34.7 g of the title compound, which was used in subsequent reactions without further purification.

EXAMPLE 4

N-(4-methoxy-4-oxobutyl)-L-phenylalaninamide monohydrochloride

The title compound was prepared by the methods of Examples 1 and 3 using methyl 4-aminobutanoate hydrochloride and was used in subsequent reactions without further purification.

EXAMPLE 5

N-(5-methoxy-5-oxopentyl)-L-phenylalaninamide monohydrochloride

The title compound was prepared by the method of Example 3 using the title compound of Example 1 and was used in subsequent reactions without further purification.

EXAMPLE 6

N-(7-methoxy-7-oxoheptyl)-L-phenylalaninamide monohydrochloride

The title compound was prepared by the methods of Examples 1 and 3 using methyl 7-aminoheptanoate hydrochloride and was used in subsequent reactions without further purification.

EXAMPLE 7

N-(8-methoxy-8-oxooctyl)-L-phenylalaninamide monohydrochloride

The title compound was prepared by the methods of Examples 1 and 3 using methyl 8-aminooctanoate hydrochloride and was used in subsequent reactions without further purification.

EXAMPLE 8 t-butoxycarbonyl-D-methionylglycine methyl ester

The title compound was prepared by the general method of Example 1 using 24.9 g (0.1 mole) of t-butoxycarbonyl-D-methionine (BOC-D-Met) and 13.8 g (0.11 mole) of glycine methyl ester hydrochloride. The crude product was recrystallized from ethyl acetate/Skellysolve B to give the title compound, which was used in subsequent reactions without further purification.

EXAMPLE 9 t-butoxycarbonyl-D-methionylglycine

The title compound of Example 8 (32.0 g, 0.1 mole) was dissolved in 200 ml of methanol to which was added 200 ml of 2 M potassium hydroxide. After ca. 5 min. at room temperature the solution was concentrated to about half volume and diluted with ethyl acetate. The solution was neutralized by washing with two portions of 0.5 M potassium bisulfate, and then dried over magnesium sulfate, filtered, and concentrated in vacuo. The crude product was recrystallized to give the title compound, which was used in subsequent reactions without further purification.

EXAMPLE 10 t-butoxycarbonyl-D-methionylglycyl-N-(6-methoxy-6-oxohexyl)-L-phenylalaninamide

A mixture of the title compounds of Example 3 (28.9 g, 0.088 mole) and Example 9 (27.2 g, 0.084 mole) in 150 ml of dichloromethane was solubilized by warming and adding 9.8 ml (ca. 0.087 mole) of N-methylmorpholine. After the solution was cooled to ca. 0°, 18.2 g (0.088 mole) of dicyclohexylcarbodiimide in 50 ml of dichloromethane was added, and the reaction mixture was allowed to warm to room temperature. After a total of four hours, insolubles were removed by filtration and the filtrate was washed sequentially with two portions of 0.5 M potassium bisulfate. The organic phase was dried over magnesium sulfate, filtered, and concentrated in vacuo. The crude material was purified by column chromatography on silica gel to give the title compound (42.0 g).

Analysis. Calcd. for $C_{28}H_{44}N_4O_7S$: C, 57.91; H, 7.64; N, 9.65; S, 5.52. Found: C, 57.84; H, 7.75; N, 9.89; S, 5.55.

EXAMPLE 11

D-methionylglycyl-N-(6-methoxy-6-oxohexyl)-L-phenylalaninamide monohydrochloride hemihydrate The title compound of Example 10 (12.0 g) was dissolved in 50 ml of dioxane to which was added 50 ml of 6 M hydrogen chloride/dioxane. After about one hour, the volatiles were removed in vacuo and the residue triturated thoroughly with diethyl ether. The title compound (10.9 g) was collected as an analytically pure hydrochloride hemihydrate.

Analysis. Calcd. for $C_{23}H_{36}N_4O_5S.HCl.\frac{1}{2}H_2O$: C, 52.51; H, 7.28; N, 10.65; S, 6.09; Cl, 6.74. Found: C, 52.33; H, 7.24; N, 10.68; S, 6.14; Cl, 6.69.

EXAMPLE 12 t-butoxycarbonyl-2,6-dimethyltyrosine

To a stirred solution of 100 g (820 mmole) of 3,5-dimethylphenol and 79 g (1 mole) of pyridine in 300 ml of cooled (5°–10°) toluene was slowly added 109 g (1 mole) of ethyl chloroformate in 100 ml of toluene. After overnight stirring, the mixture was concentrated in vacuo to an oil which was purified by distillation at reduced pressure, giving an intermediate carbonate diester. After heating 250 ml of concentrated hydrochloric acid to ca. 55°, 22 g of 37% aqueous formaldehyde was added, followed by addition of the carbonate diester. Hydrogen chloride gas was bubbled through the solution for about six hours. The mixture was allowed to stand overnight at room temperature and then shaken with dichloromethane. The organic phase thus formed was washed with water, aqueous sodium bicarbonate, and saturated brine, and then dried over sodium sulfate, filtered, and concentrated in vacuo. The resultant 4-chloromethyl derivative was purified by distillation at reduced pressure. After preparing an ethanolic solution of sodium ethoxide from 2.5 g (110 mmole) of sodium metal, 21.7 g (100 mmole) of diethyl acetamidomalonate was added and the solution heated to reflux. An ethanolic solution of the 4-chloromethyl intermediate was then added and the mixture was heated at reflux for another 2.5 hours. After standing overnight at room temperature, the mixture was treated with 6.6 g (110 mmole) of acetic acid. The resultant gum was dissolved in dichloromethane, which was then washed with aqueous sodium bicarbonate, filtered, and concentrated in vacuo to an oily residue. Recrystallization from diethyl ether afforded 6.5 g of the benzyl malonate derivative (from which the O-ethyoxycarbonyl group was lost). Heating a 1.0 g portion of the malonate derivative in concentrated hydrochloric acid at 95° for about three days afforded 680 mg of 2,6-dimethyltyrosine as the nearly analytically pure hydrated hydrochloride salt. [Analysis. Calcd. for $C_{11}H_{15}NO_3.HCl.H_2O$: C, 50.09; H, 6.13; N, 5.31; Cl, 13.44. Found: C, 49.36; H, 6.30; N, 5.20; Cl, 14.10.] About 45 g of the amino acid prepared as above was then dissolved in ca. 400 ml of ice water, which was adjusted to about pH 10. Di-t-butyl dicarbonate (41 g) was added, with maintenance of pH to 13 to saponify O-butoxycarbonyl groups, the mixture was cooled to about 0° and adjusted to pH 2. The crude title compound was extracted into ethyl acetate, which was washed with saturated brine, dried over sodium sulfate, filtered, and dried under a stream of nitrogen. Recrystallization from ethyl acetate afforded analytically pure BOC-protected compound.

Analysis. Calcd. for $C_{16}H_{23}NO_5$: C, 62.12; H, 7.49; N, 4.53. Found: C, 61.87; H, 7.51; N, 4.34.

EXAMPLE 13 t-butoxycarbonyl-2,6-dimethyl-(D and L)-tyrosyl-D-methionylglycyl-N-(6-methoxy-6-oxohexyl)-L-phenylalaninamide The title compound was prepared by the method of Example 1 using 6.80 g (0.022 mole) of t-butoxycarbonyl-2,6-dimethyltyrosine and the title compound of Example 11 (10.8 g, 0.020 mole). A portion of the crude racemic product (4.5 g) was purified by column chromatography on silica gel (methanol/chloroform eluent) to give 1.79 g of the D isomer and 2.11 g of the L isomer. The individual isomeric components, differing in the alpha-carbon stereochemistry of the 2,6-dimethyl-tyrosine moiety, were used without further purification in subsequent reactions.

EXAMPLE 14

2,6-dimethyl-L-tyrosyl-D-methionylglycyl-N-(6-methoxy-6-oxohexyl)-L-phenylalaninamide monohydrochloride monohydrate (SC-36739)

The L isomer of the title compound of Example 13 (2.11 g) was dissolved in 20 ml of acetic acid to which was added 20 ml of 6 M hydrogen chloride/dioxane. After one hour at room temperature, volatiles were removed in vacuo and the residue triturated thoroughly with diethyl ether. The title compound was collected as 1.95 g of an analytically pure solid.

$[\alpha]_D$ +5.3°; $[\alpha]_{365}$ +187.8° (methanol)

Analysis. Calcd. for $C_{34}H_{49}N_5O_7S.HCl.H_2O$: C, 56.23; H, 7.22; N, 9.64; S, 4.41; Cl, 4.88. Found: C, 56.19; H, 7.04; N, 9.57; S, 4.33; Cl, 4.99.

EXAMPLE 15

2,6-dimethyl-D-tyrosyl-D-methionylglycyl-N-(6-methoxy-6-oxohexyl)-L-phenylalaninamide monohydrochloride monohydrate (SC-36738)

The title compound was prepared by the method of Example 14 using the D isomer of Example 13.

Analysis. Calcd. for $C_{34}H_{49}N_5O_7S.HCl.H_2O$: C, 56.23; H, 7.22; N, 9.64; S, 4.41; Cl, 4.88. Found: C, 56.19; H, 7.04; N, 9.57; S, 4.33; Cl, 4.99.

$[\alpha]_D$ −51.1°; $[\alpha]_{365}$

EXAMPLE 16

2,6-dimethyl-L-tyrosyl-[4-(methylsulfinyl)-D-2-aminobutanoyl]glycyl-N-(6-methoxy-6-oxohexyl)-L-phenylalaninamide monohydrochloride 2½ hydrate (SC-36755)

To a solution of the title compound of Example 14 (0.71 g, 1.0 mmole) in 3.5 ml of water and 3.5 ml of methanol was added 0.5 ml of 10 M hydrogen peroxide. After one hour at room temperature, the reaction was diluted with water to about 70 ml, filtered, and the filtrate lyophilized. The title compound (0.68 g) was isolated as an analytically pure hydrated solid.

$[\alpha]_D$ +46.7°; $[\alpha]_{365}$ +172.0° (methanol)

Analysis. Calcd. for $C_{34}H_{49}N_5O_8S.HCl.2½ H_2O$: C, 53.08; H, 7.20; N, 9.10; S, 4.17; Cl, 4.61. Found: C, 52.78; H, 6.57; N, 8.95; S, 4.35; Cl, 4.70.

EXAMPLE 17

2,6-dimethyl-D-tyrosyl-[4-(methylsulfinyl)-D-2-aminobutanoyl]glycyl-N-(6-methoxy-6-oxohexyl)-L-phenylalaninamide monohydrochloride 2½ hydrate (SC-36773)

The title compound was prepared by the method of Example 16 using the title compound of Example 15.

Analysis. Calcd. for $C_{34}H_{49}N_5O_8S.HCl.2½ H_2O$: C, 53.08; H, 7.20; N, 9.10; S, 4.17; Cl, 4.61. Found: C, 52.96; H, 6.71; N, 9.04; S, 4.24; Cl, 4.55.

EXAMPLE 18

2,6-dimethyltyrosyl-[4-(methylsulfinyl)-D-2-aminobutanoyl]glycyl-N-(6-methoxy-6-oxohexyl)-L-phenylalaninamide monohydrochloride sesquihydrate (SC-34973)

The title compound was prepared from an unresolved mixture of the compound mixture of Example 13 using the methods of Examples 14 and 16.

Analysis. Calcd. for $C_{34}H_{49}N_5O_8S.HCl.3/2H_2O$: C, 54.35; H, 7.11; N, 9.32; S, 4.27; Cl, 4.72. Found: 54.20; H, 6.80; N, 9.23; S, 4.17; Cl, 4.70.

EXAMPLE 19

2,6-dimethyl-L-tyrosyl-D-methionylglycyl-N-(5-methoxy-5-oxopentyl)-L-phenylalaninamide monohydrochloride monohydrate (SC-36589)

The title compound was prepared by the methods of Examples 10, 11, 13, and 14 using the title compound of Example 5.

Analysis. Calcd. for $C_{33}H_{47}N_5O_7S.HCl.H_2O$: 55.65; H, 7.08; N, 9.83; S, 4.50; Cl, 4.98.

Found: S, 56.00; H, 7.06; N, 9.61; S, 4.09; Cl, 5.01.

EXAMPLE 20

2,6-dimethyl-D-tyrosyl-D-methionylglycyl-N-(5-methoxy-5-oxopentyl)-L-phenylalaninamide monohydrochloride monohydrate (SC-36588)

The title compound was prepared by the methods of Examples 10, 11, 13, and 15 using the title compound of Example 5.

Analysis. Calcd. for $C_{33}H_{47}N_5O_7S.HCl.H_2O$; C, 55.65; H, 7.08; N, 9.83; S, 4.50; Cl, 4.98. Found: C, 55.84; H, 7.03; N, 9.77; S, 4.43; Cl, 5.21.

EXAMPLE 21

2,6-dimethyl-L-tyrosyl-[4-methylsulfinyl)-D-2-aminobutanoyl]glycyl-N-(5-methoxy-5-oxopentyl)-L-phenylalaninamide monohydrochloride 2½ hydrate (SC-36655)

The title compound was prepared by the method of Example 16 using the title compound of Example 19.

Analysis. Calcd. for $C_{33}H_{47}N_5O_8S.HCl.2½ H_2O$: C, 52.48; H, 4.07; N, 9.27; S, 4.25; Cl, 4.69. Found: C, 52.31; H, 6.58; N, 9.16; S, 4.30.

Example 22

2,6-dimethyl-D-tyrosyl-[4-methylsulfinyl)-D-2-aminobutanoyl]glycyl-N-(5-methoxy-5-oxopentyl)-L-phenylalaninamide monohydrochloride The title compound is prepared by the method of Example 16 using the title compound of Example 20.

EXAMPLE 23

2,6-dimethyl-L-tyrosyl-D-methionylglycyl-N-(7-methoxy-7-oxoheptyl)-L-phenylalaninamide monohydrochloride monohydrate (SC-36777)

The title compound was prepared by the methods of Examples 10, 11, 13, and 14 using the title compound of Example 6.

Analysis. Calcd. for $C_{35}H_{51}N_5O_7S.HCl.H_2O$: C, 56.78; H, 7.35; N, 9.46; S, 4.33; Cl, 4.79. Found: C, 56.84; H, 7.07; N, 9.60.

EXAMPLE 24

2,6-dimethyl-D-tyrosyl-D-methionylglycyl-N-(7-methoxy-7-oxoheptyl)-L-phenylalaninamide monohydrochloride hemihydrate (SC-36776)

The title compound was prepared by the methods of Examples 10, 11, 13, and 15 using the title compound of Example 6.

Analysis. Calcd. for $C_{35}H_{51}N_5O_7S.HCl.½H_2O$: C, 57.48; H, 7.30; N, 9.58; S, 4.38; Cl, 4.85. Found: C, 57.36; H, 7.11; N, 9.61.

EXAMPLE 25

2,6-dimethyl-L-tyrosyl-[4-(methylsulfinyl)-D-2-aminobutanoyl]glycyl-N-(7-methoxy-7-oxoheptyl)-L-phenylalaninamide monohydrochloride (SC-36922)

The title compound was prepared by the method of Example 16 using the title compound of Example 23.

Analysis. Calcd. for $C_{35}H_{51}N_5O_8S.HCl$: C, 54.93; H, 7.24; N, 9.15; S, 4.19; Found: C, 54.96; H. 6.96; N, 9.17; S, 4.19.

EXAMPLE 26

2,6-dimethyl-D-tyrosyl-[4-(methylsulfinyl)-D-2-aminobutanoyl]glycyl-N-(7-methoxy-7-oxoheptyl)-L-phenylalaninamide monohydrochloride sesquihydrate (SC-36921)

The title compound was prepared by the method of Example 16 using the title compound of Example 24.

Analysis. Calcd. for $C_{35}H_{51}N_5O_8S \cdot HCl \cdot 3/2H_2O$: C, 54.93; H, 7.24; N, 9.15; S, 4.19; Cl, 4.63. Found: C, 54.57; H, 6.92; N, 9.08; S, 3.83.

EXAMPLE 27

2,6-dimethyl-L-tyrosyl-D-methionylglycyl-N-(8-methoxy-8-oxooctyl)-L-phenylalaninamide monohydrochloride hemihydrate (SC-36338)

The title compound was prepared by the method of Examples 10, 11, 13, and 14 using the title compound of Example 7.

Analysis. Calcd. for $C_{36}H_{53}N_5O_7S \cdot HCl \cdot \frac{1}{2} H_2O$: C, 58.01; H, 7.44; N, 9.40; S, 4.41; Found: C, 57.85; H, 7.68; N, 9.40; S, 5.22.

EXAMPLE 28

2,6-dimethyl-D-tyrosyl-D-methionylglycyl-N-(8-methoxy-8-oxooctyl)-L-phenylalaninamide monohydrochloride monohydrate (SC-36337)

The title compound was prepared by the methods of Examples 10, 11, 13, and 15 using the title compound of Example 7.

Analysis Calcd. for $C_{36}H_{53}N_5O_7S \cdot HCl \cdot H_2O$: C, 57.32; H, 7.48; N, 9.28; Cl, 4.70. Found: C, 57.33; H, 7.51; N, 9.13; Cl, 5.41.

EXAMPLE 29

2,6-dimethyl-L-tyrosyl-[4-(methylsulfinyl)-D-2-aminobutanoyl]glycyl-N-(8-methoxy-8-oxooctyl)-L-phenylalaninamide monohydrochloride monohydrate (SC-36344)

The title compound was prepared by the methods of Example 15 using the title compound of Example 27.

Analysis. Calcd. for $C_{36}H_{53}N_5O_8S \cdot HCl \cdot H_2O$: C, 56.13; H, 7.33; N, 9.09; Cl, 4.60. Found: C, 56.04; H, 7.22; N, 9.06, Cl, 4.81.

EXAMPLE 30

2,6-dimethyl-D-tyrosyl-[4-(methylsulfinyl)-D-2-aminobutanoyl]glycyl-N-(8-methoxy-8-oxooctyl)-L-phenylalaninamide monohydrochloride monohydrate (SC-36392)

The title compound was prepared by the method of Example 16 using the title compound of Example 28.

Analysis. Calcd. for $C_{36}H_{53}N_5O_8S \cdot HCl \cdot H_2O$: C, 56.13; H, 7.33; N, 9.09; Found: C, 55.76; H, 7.18; N, 9.02.

EXAMPLE 31

2,6-dimethyltyrosyl-[4-(methylsufinyl)-D-2-aminobutanoyl]glycyl-N-(4-methoxy-4-oxobutyl)-L-phenylalaninamide monohydrochloride sesquihydrate (SC-34972)

The title compound was prepared by the methods of Examples 10, 11, 13 (except that the racemic mixture was not resolved), 14, and 16 using the title compound of Example 4.

Analysis. Calcd. for $C_{32}H_{45}N_5O_8S \cdot HCl \cdot 3/2H_2O$: C, 53.14; H, 6.83; N, 9.68; S, 4.43; Cl, 4.90. Found: C, 53.27; H, 6.55; N, 9.34; S, 4.42; Cl, 5.37.

EXAMPLE 32

L-tyrosyl-D-methionylgycyl-N-(6-methoxy-6-oxohexyl)-L-phenylalaninamide monohydrochloride sesquihydrate (SC-36798)

The title compound was prepared using the methods of Examples 13 and 14 using t-butoxycarbonyltyrosine in place of t-butoxycarbonyl-2,6-dimethyltyrosine. Structure assignment was supported by elemental analysis.

Analysis. Calcd. for $C_{32}H_{45}N_5O_7S \cdot HCl \cdot 3/2H_2O$: C, 54.34; H, 6.98; N, 9.90; S, 4.53; Cl, 5.01. Found: C, 54.30; H, 6.61; N, 9.82; S, 4.19; Cl, 5.61.

EXAMPLE 33

L-tyrosyl-[4-(methylsulfinyl)-D-2-aminobutanoyl]glycyl-N-(6-methoxy-6-oxohexyl)-L-phenylalaninamide monohydrochloride monohydrate (SC-36801)

The title compound was prepared by the method of Example 16 using the title product of Example 32. Structure assignment was supported by elemental analysis.

Analysis. Calcd. for $C_{32}H_{45}N_5O_8S \cdot HCl \cdot H_2O$: C, 53.81; H, 6.77; N, 9.81; S, 4.49; Cl, 5.21. Found: C, 53.46; H, 6.55; N, 9.80; S, 4.23; Cl, 5.21.

EXAMPLE 34

$N^\alpha$-methyl-L-tyrosyl-D-methionylglycyl-N-(6-methoxy-6-oxohexyl)-L-phenylalaninamide monohydrochloride hemihydrate (SC-36814)

The title compound was prepared using the methods of Examples 13 and 14 using t-butoxycarbonyl-N-methyltyrosine in place of t-butoxycarbonyl-2,6-dimethyltyrosine. Structure assignment was supported by elemental analysis.

Analysis. Calcd. for $C_{33}H_{47}N_5O_7S \cdot HCl \cdot H_2O$: C, 56.36; H, 7.02; N, 9.96; S, 4.07; Cl, 5.04. Found: C, 56.21; H, 6.90; N, 9.81; S, 4.47; Cl, 5.14.

EXAMPLE 35

N$\alpha$-methyl-L-tyrosyl-[4-(methylsulfinyl)-D-2-aminobutanoyl]glycyl-N-(6-methoxy-6-oxohexyl)-L-phenylalaninamide monohydrochloride 1¼ hydrate (SC-36816)

The title compound was prepared by the method of Example 16 using the title product of Example 34. Structure assignment was supported by elemental analysis.

Analysis. Calcd. for $C_{33}H_{47}N_5O_8S \cdot HCl \cdot \frac{1}{4}H_2O$: C, 54.09; H, 6.95; N, 9.56; S, 4.37; Cl, 4.84. Found: C, 53.96; H, 6.69; N, 9.53; S, 4.26; Cl, 4.95.

EXAMPLE 36 t-butoxycarbonyl-3-cyclohexyl-L-alanine

A solution of 30.0 g (0.11 mole) of t-butoxycarbonylphenylalanine in 750 ml of tetrahydrofuran was hydrogenated at 60° for 24 hours using 50 psi hydrogen gas and 5% rhodium on carbon. The mixture was filtered and the filtrate concentrated to give the title compound (30.7 g) as a colorless oil. The oil was used without further purification. Structure assignment was supported by the nmr spectrum (loss of aromatic protons and appearance of cyclohexyl protons).

EXAMPLE 37

2,6-dimethyl-L-tyrosyl-D-methionylglycyl-N-(6-methoxy-6-oxohexyl)-3-cyclohexyl-L-alaninamide monohydrochloride hemihydrate (SC-37990)

After preparing N-(6-methoxy-6-oxohexyl)-3-cyclohexyl-Lalaninamide monohydrochloride from the title product of Example 36 by the methods of Examples 1 and 3, the title compound was prepared by the methods described in Examples 10, 11, 13, and 14. Structure assignment was supported by elemental analysis.

Analysis Calcd for $C_{34}H_{55}N_5O_7S.HCl.\frac{1}{2}H_2O$: C, 56.46; H, 7.94; N, 9.68; S, 4.43; Cl, 4.90. Found: C, 56.07; H, 7.78; N, 9.42; S, 4.38; Cl, 5.21.

EXAMPLE 38

2,6-dimethyl-D-tyrosyl-D-methionylglycyl-N-(6-methoxy-6-oxohexyl)-3-cyclohexyl-L-alaninamide monohydrochloride hemihydrate (SC-37989)

The title compound was prepared by the methods summarized in Example 37, except for using the method of Example 15 instead of Example 14. Structure assignment was supported by elemental analysis.

Analysis. Calcd. for $C_{34}H_{55}N_5O_7S.HCl.\frac{1}{2}H_2O$: C, 56.46; H, 7.94; N, 9.68; S, 4.43; Cl, 4.90. Found: C, 56.34; H, 7.87; N, 9.59; S, 4.46; Cl, 5.14.

EXAMPLE 39

2,6-dimethyl-L-tyrosyl-[4-(methylsulfinyl)-D-2-aminobutanoyl]glycyl-N-(6-methoxy-6-oxohexyl)-3-cyclohexyl-L-alaninamide monohydrochloride dihydrate (SC-39029)

The title compound was prepared by the method of Example 16 using the title product of Example 37. Structure assignment was supported by elemental analysis.

Analysis. Calcd. for $C_{34}H_{55}N_5O_8S.HCl.2H_2O$: C, 53.29; H, 7.89; N, 9.14; S, 4.18; Cl, 4.63. Found: C, 53.11; H, 7.47; N, 9.02; S, 4.25; Cl, 4.86.

EXAMPLE 40

2,6-dimethyl-D-tyrosyl-[4-(methylsulfinyl)-D-2-aminobutanoyl]glycyl-N-(6-methoxy-6-oxohexyl)-3-cyclohexyl-L-alaninamide monohydrochloride dihydrate (SC-39028)

The title compound was prepared by the method of Example 16 using the title product of Example 38. Structure assignment was supported by elemental analysis.

Analysis. Calcd. for $C_{34}H_{55}N_5O_8S.HCl.2H_2O$: C, 53.29; H, 7.89; N, 9.14; S, 4.18; Cl, 4.63. Found: C, 52.91; H, 7.43; N, 8.96; S, 4.24; Cl, 4.72.

EXAMPLE 41

L-tyrosyl-D-methionylglycyl-N-(6-methoxy-6-oxohexyl)-3-cyclohexyl-L-alaninamide monohydrochloride monohydrate (SC-39564)

The title compound was prepared by the method of Example 37 using t-butoxycarbonyltyrosine in place of t-butoxycarbonyl-2,6-dimethyltyrosine. Structure assignment was supported by elemental analysis.

Analysis. Calcd. for $C_{32}H_{51}N_5O_7S.HCl.H_2O$: C, 54.47; H, 7.73; N, 9.94; S, 4.55; Cl, 5.03. Found: C, 54.84; H, 7.65; N, 9.84; S, 4.56; Cl, 5.18.

EXAMPLE 42 t-butoxycarbonyl-3-cyclohexyl-N-methyl-L-alanine

A solution of 4.8 g of t-butoxycarbonyl-N-methylphenylalanine in 150 ml of tetrahydrofuran was hydrogenated at 60° for about four days using 60 psi hydrogen gas and 5% rhodium on carbon. The mixture was filtered and the filtrate concentrated to give the title compound (3.5 g) as a colorless oil. The oil was used without further purification. Structure assignment was supported by the nmr spectrum (loss of aromatic protons and appearance of cyclohexyl protons) and by elemental analysis.

Analysis. Calcd. for $C_{15}H_{27}NO_4$: C, 63.13; H, 9.54; N, 4.91. Found: C, 63.72; H, 9.88; N, 4.68.

EXAMPLE 43

2,6-dimethyl-L-tyrosyl-D-methionylglycyl-N-(6-methoxy-6-oxohexyl)-3-cyclohexyl-$N^\alpha$-methyl-L-alaninamide monohydrochloride (SC-40894)

After preparing N-(6-methoxy-6-oxohexyl)-3-cyclohexyl-$N^\alpha$-methyl-L-alaninamide monohydrochloride from the title product of Example 42 by the methods of Examples 1 and 3, the title compound was prepared by the methods described in Examples 10, 11, 13, and 14. Structure assignment was supported by elemental analysis.

Analysis. Calcd. for $C_{35}H_{57}N_5O_7S.HCl.\frac{3}{8}H_2O$: C, 56.78; H, 8.08; N, 9.46; S, 4.33; Cl, 4.79. Found: C, 56.63; H, 7.92; N, 9.42; S, 4.32; Cl, 4.99.

EXAMPLE 44

2,6-dimethyl-D-tyrosyl-D-methionylglycyl-N-(6-methoxy-6-oxohexyl)-3-cyclohexyl-$N^\alpha$-methyl-L-alaninamide monohydrochloride (SC-40892)

The title compound was prepared by the methods summarized in Example 43, except for using the method of Example 15 instead of Example 14. Structure assignment was supported by elemental analysis.

Analysis. Calcd. for $C_{35}H_{57}N_5O_7S.HCl.\frac{3}{8}H_2O$: C, 56.78; H, 8.08; N, 9.46; S, 4.33; Cl, 4.79. Found: C, 56.83; H, 7.99; N, 9.48; S, 4.30; Cl, 5.04.

EXAMPLE 45

2,6-dimethyl-L-tyrosyl-[4-(methylsulfinyl)-D-2-aminobutanoyl]glycyl-N-(6-methoxy-6-oxohexyl)-3-cyclohexyl-$N^\alpha$-methyl-L-alaninamide monohydrochloride The title compound is prepared by the method of Example 16 using the title product of Example 43.

EXAMPLE 46

2,6-dimethyl-D-tyrosyl-[4-(methylsulfinyl)-D-2-aminobutanoyl]glycyl-N-(6-methoxy-6oxohexyl)-3-cyclohexyl-$N^\alpha$-methyl-L-alaninamide monohydrochloride The title compound is prepared by the method of Example 16 using the title product of Example 44.

EXAMPLE 47 t-butoxycarbonyl-2,4,6-trimethylphenylalanine

After preparing an ethanolic solution of sodium ethoxide from 30.1 g (1.31 mole) of sodium metal, 200 g (1.19 mole) of diethyl acetamidomalonate was added and the solution heated to reflux. An ethanolic solution of the 2,4,6-trimethylbenzyl chloride was then added and the mixture was heated at reflux for another four hours. The mixture was concentrated in vacuo and the residue triturated multiply with water, then with dichloromethane. After removing insolubles by filtration, the filtrate was washed with brine, decolorized with activated carbon, filtered, concentrated to a small volume, and allowed to stand. Repetition of the decolorization, followed by recrystallization from Skellysolve B afforded the analytically pure benzyl malonate derivative. A portion of the malonate (12 g, 36 mmole) was heated at reflux in a mixture of 50 ml ethanol and 50 ml concentrated hydrochloric acid for about four days. Upon cooling, racemic 2,4,6-trimethylphenylalanine precipitated. The BOC-protected title compound was prepared using di-t-butyl dicarbonate as described in Example 12.

EXAMPLE 48

2,6-dimethyl-L-tyrosyl-D-methionylglycyl-N-(6-methoxy-6-oxohexyl)-2,4,6-trimethylphenylalaninamide monohydrochloride monohydrate (SC-39724)

After preparing N-(6-methoxy-6-oxohexyl)-2,4,6-trimethylphenylalaninamide monohydrochloride from the title product of Example 47 by the methods of Examples 1 and 3, the title compound was prepared by the methods described in Examples 10, 11, 13, and 14. Structure assignment was supported by elemental analysis.

Analysis. Calcd. for $C_{37}H_{55}N_5O_7S\cdot HCl\cdot H_2O$: C, 57.84; H, 7.61; N, 9.11; S, 4.17; Cl, 4.61. Found: C, 58.12; H, 7.55; N, 8.96; S, 4.13; Cl, 5.07.

EXAMPLE 49

2,6-dimethyl-D-tyrosyl-D-methionylglycyl-N-(6-methoxy-6-oxohexyl)-2,4,6-trimethylphenylalaninamide monohydrochloride hemihydrate (SC-39699)

The title compound was prepared by the methods summarized in Example 48, except for using the method of Example 15 instead of Example 14. Structure assignment was supported by elemental analysis.

Analysis. Calcd. for $C_{37}H_{55}N_5O_7S\cdot HCl\cdot \frac{1}{2}H_2O$: C, 58.52; H, 7.57; N, 9.22; S, 4.22; Cl, 4.67. Found: C, 58.44; H, 7.58; N, 8.88; S, 4.19; Cl, 4.94.

EXAMPLE 50

2,6-dimethyl-L-tyrosyl-[4-(methylsulfinyl)-D-2-aminobutanoyl]glycyl-N-(6-methoxy-6-oxohexyl)-2,4,6-trimethylphenylalaninamide monohydrochloride sesquihydrate (SC-40178)

The title compound was prepared by the method of Example 16 using the title product of Example 48. Structure assignment was supported by elemental analysis.

Analysis. Calcd. for $C_{37}H_{55}N_5O_8S\cdot HCl\cdot 3/2H_2O$: C, 56.01; H, 7.50; N, 8.83; S, 4.04; Cl, 4.47. Found: C, 58.84; H, 7.20; N, 8.80; S, 4.01; Cl, 4.56.

EXAMPLE 51

2,6-dimethyl-D-tyrosyl-[4-(methylsulfinyl)-D-2-aminobutanoyl]glycyl-N-(6-methoxy-6oxohexyl)-2,4,6-trimethylphenylalaninamide monohydrochloride sesquihydrate (SC-40075)

The title compound was prepared by the method of Example 16 using the title product of Example 49. Structure assignment was supported by elemental analysis.

Analysis. Calcd. for $C_{37}H_{55}N_5O_8S\cdot HCl\cdot 3/2H_2O$: C, 56.01; H, 7.50; N, 8.83; S, 4.04; Cl, 4.47. Found: C, 56.23; H, 7.32; N, 8.78; S, 4.16; Cl, 4.60.

EXAMPLE 52

2,6-dimethyl-L-tyrosyl-D-methionylglycyl-N-(6-methoxy-6-oxohexyl)-N-methyl-3-cyclohexyl-L-alaninamide monohydrochloride hemihydrate (SC-40869)

After preparing N-(6-methoxy-6-oxohexyl)-N-methyl-3-cyclohexyl-L-alaninamide monohydrochloride from methyl 6-(methylamino)hexanoate and the title product of Example 36 by the methods of Examples 1 and 10, the title compound was prepared by the methods described in Examples 10, 11, 13, and 14. Structure assignment was supported by elemental analysis.

Analysis. Calcd. for $C_{35}H_{57}N_5O_7S\cdot HCl\cdot \frac{1}{2}H_2O$: C, 57.01; H, 8.06; N, 9.50; S, 4.35; Cl, 4.81. Found: C, 56.96; H, 8.10; N, 9.53; S, 4.36; Cl, 4.94.

EXAMPLE 53

2,6-dimethyl-D-tyrosyl-D-methionylglycyl-N-(6-methoxy-6-oxohexyl)-N-methyl-3-cyclohexyl-L-alaninamide monohydrochloride hemihydrate (SC-40810)

The title compound was prepared by the methods summarized in Example 52, except for using the method of Example 15 instead of Example 14. Structure assignment was supported by elemental analysis.

Analysis. Calcd. for $C_{35}H_{57}N_5O_7S\cdot HCl\cdot \frac{1}{2}H_2O$: C, 57.01; H, 8.06; N, 9.50; S, 4.35; Cl, 4.81. Found: C, 56.98; H, 7.99; N, 9.21; S, 4.27; Cl, 4.90.

EXAMPLE 54

2,6-dimethyl-L-tyrosyl-[4-(methylsulfinyl)-D-2-aminobutanoyl]glycyl-N-(6-methoxy-6oxohexyl)-N-methyl-3-cyclohexyl-L-alaninamide monohydrochloride The title compound is prepared by the method of Example 16 using the title product of Example 52.

EXAMPLE 55

2,6-dimethyl-D-tyrosyl-[4-(methylsulfinyl)-D-2-aminobutanoyl]glycyl-N-(6-methoxy-6oxohexyl)-N-methyl-3-cyclohexyl-L-alaninamide monohydrochloride The title compound is prepared by the method of Example 16 using the title product of Example 53.

EXAMPLE 56

2,6-dimethyl-L-tyrosyl-D-methionylglycyl-N-(6-hydroxyhexyl)-L-phenylalaninamide monohydrochloride monohydrate (SC-39782)

Using 6-aminohexanol instead of an omega-aminoalkanoic acid, t-butoxycarbonyl-N-(6-hydroxyhexyl)-L-phenylalaninamide was prepared by the general method of Example 1. Using the method of Example 3, except for adding about an equal volume of acetic acid to facilitate solution, the N-protected precursor was converted to N-(6-acetyloxyhexyl)-L-phenylalaninamide. After then proceeding by the methods of Examples 10, 11, and 13, the intermediate terminal O-acetyl group was removed by the method of Example 9. Finally, the title compound was prepared using the method of Example

EXAMPLE 57

2,6-dimethyl-D-tyrosyl-D-methionylglycyl-N-(6-hydroxyhexyl)-L-phenylalaninamide monohydrochloride monohydrate (SC-39781)

The title compound was prepared by the methods summarized in Example 56, except for using the method of Example 15 instead of Example 11 in the final step. Structure assignment was supported by elemental analysis.
Analysis. Calcd. for $C_{33}H_{49}N_5O_6S.HCl.H_2O$:
C, 56.76; H, 7.50; N, 10.03; S, 4.59; Cl, 5.08.
Found: C, 56.40; H, 7.48; N, 9.75; S, 4.41; Cl, 5.53.

EXAMPLE 58 cl 2,6-dimethyl-L-tyrosyl-[4-(methylsulfinyl)-D-2-aminobutanoyl]glycyl-N-(6-hydroxyhexyl)-L-phenylalaninamide monohydrochloride sesquihydrate (SC-40238)

The title compound was prepared by the method of Example 16 using the title product of Example 56. Structure assignment was supported by elemental analysis.
Analysis. Calcd. for $C_{33}H_{49}N_5O_7S.HCl.3/2H_2O$:
C, 54.87; H, 7.26; N, 9.70; S, 4.44; Cl, 4.91.
Found: C, 54.57; H, 6.76; N, 9.41; S, 4.30; Cl, 5.12.

EXAMPLE 59

2,6-dimethyl-D-tyrosyl-[4-(methylsulfinyl)-D-2-aminobutanoyl]glycyl-N-(6-hydroxyhexyl)-L-phenylalaninamide monohydrochloride dihydrate (SC-40192)

The title compound was prepared by the method of Example 16 using the title product of Example 57. Structure assignment was supported by elemental analysis.
Analysis. Calcd. for $C_{33}H_{49}N_5O_7S.HCl.2H_2O$:
C, 54.12; H, 7.43; N, 9.56; S, 4.38; Cl, 4.84.
Found: C, 54.32; H, 6.79; N, 9.47; S, 4.31; Cl, 5.17.

EXAMPLE 60

2,6-dimethyl-L-tyrosyl-D-methionylglycyl-N-(6-acetyloxyhexyl)-$N^\alpha$-methyl-L-phenylalanin-amide monohydrochloride hemihydrate (SC-39745)

The title compound was prepared by the methods summarized in Example 56, except that t-butoxycarbonyl-N--methyl-L-phenylalanine was used instead of t-butoxycarbonylphenylalanine and the O-acetyl group was not removed before proceeding to the final reaction, which employed the method of Example 14. Structure assignment was supported by elemental analysis.
Analysis Calcd. for $C_{36}H_{53}N_5O_7S.HCl.\frac{1}{2}H_2O$:
C, 58.01; H, 7.30; N, 9.40; S, 4.30; Cl, 4.76.
Found: C, 57.67; H, 7.21; N, 9.33; S, 4.46; Cl, 5.10.

EXAMPLE 61

2,6-dimethyl-D-trosyl-D-methionylglcyl-N-(6-acetyloxyhexyl)-$N^\alpha$-methyl-L-phenylalaninamide monohydrochloride monohydrate (SC-39734)

The title compound was prepared by the methods of Example 60, except for using the method of Example 15 instead of Example 14 in the final step. Structure assignment was supported by elemental analysis.
Analysis. Calcd. for $C_{36}H_{53}N_5O_7S.HCl.H_2O$:
C, 57.32; H, 7.48; N, 9.28; S, 4.25; Cl, 4.70.
Found: C, 57.26; H, 7.24; N, 9.20; S, 4.30; Cl, 5.17.

EXAMPLE 62

2,6-dimethyl-L-tyrosyl-D-methionylglycyl-N-(6-hydroxyhexyl)-$N^\alpha$-methyl-L-phenylalaninamide hydrochloride monohydrate (SC-40061)

The title compound was prepared (as the 1.2 HCl monohydrate) from the title product of Example 60 using the method of Example 9. Structure assignment was supported by elemental analysis.
Analysis. Calcd. for $C_{34}H_{51}N_5O_6S.1.2HCl.H_2O$:
C, 56.75; H, 7.59; N, 9.73; S, 4.46; Cl, 5.91.
Found: C, 56.83; H, 7.38; N, 9.40; S, 4.36; Cl, 5.74.

EXAMPLE 63

2,6-dimethyl-D-tyrosyl-D-methionylglycyl-N-(6-hydroxyhexyl)-$N^\alpha$-methyl-L-phenylalaninamide hydrochloride monohydrate (SC-40060)

The title compound was prepared (as the 1.2 HCl monohydrate) from the title product of Example 60 using the method of Example 9. Structure assignment was supported by elemental analysis.
Analysis. Calcd. for $C_{34}H_{51}N_5O_6S.1.2HCl.H_2O$:
C, 56.75; H, 7.59; N, 9.73; S, 4.46; Cl, 5.91.
Found: 56.77; H, 7.37; N, 9.49; S, 4.45; Cl, 5.74.

EXAMPLE 64

2,6-dimethyl-L-tyrosyl-[4-(methylsulfinyl)-D-2-aminobutanoyl]glycyl-N-(6-hydroxyhexyl)-$N^\alpha$-methyl-L-phenylalaninamide monohydrochloride sesquihydrate (SC-40446)

The title compound was prepared by the method of Example 16 using the title product of Example 62. Structure assignment was supported by elemental analysis.
Analysis. Calcd. for $C_{34}H_{51}N_5O_7S.HCl.3/2H_2O$:
C, 55.38; H, 7.52; N, 9.50; S, 4.35; Cl, 4.81. Found: C, 55.38; H, 7.23; N, 9.16; S, 4.26; Cl, 5.14.

EXAMPLE 65

2,6-dimethyl-D-tyrosyl-[4-(methylsulfinyl)-D-2-aminobutanoyl]glycyl-N-(6-hydroxyhexyl)-$N^\alpha$-methyl-L-phenylalaninamide monohydrochloride dihydrate (SC-40358)

The title compound was prepared by the method of Example 16 using the title product of Example 63. Structure assignment was supported by elemental analysis.
Analysis. Calcd. for $C_{34}H_{51}N_5O_7S.HCl.2H_2O$:
C, 54.72; H, 7.56; N, 9.38; S, 4.30; Cl, 4.75.
Found: C, 54.86; H, 7.48; N, 9.46; S, 4.29; Cl, 5.00.

EXAMPLE 66

2,6-dimethyl-L-tyrosyl-D-methionylglycyl-N-(6-hydroxyhexyl)-3-cyclohexyl-$N^\alpha$-methyl-L-alaninamide monohydrochloride The title compound is prepared by the methods summarized in Example 56, except that t-butoxycarbonyl-3-cyclohexyl-N-methyl-L-alanine was used instead of t-butoxycarbonylphenylalanine (as used in Example 1).

EXAMPLE 67

2,6-dimethyl-D-tyrosyl-D-methionylglycyl-N-(6-hydroxyhexyl)-3-cyclohexyl-N$^\alpha$-methyl-L-alaninamide monohydrochloride The title compound is prepared by the methods summarized in Example 66.

Example 68

2,6-dimethyl-L-tyrosyl-[4-(methylsulfinyl)-D-2-aminobutanoyl]glycyl-N-(6-hydroxyhexyl)-3-cyclohexyl-N$^\alpha$-methyl-L-alaninamide monohydrochloride The title compound is prepared by the method of Example 16 using the title product of Example 66.

Example 69

2,6-dimethyl-D-tyrosyl-[4-(methylsulfinyl)-D-2-aminobutanoyl]glycyl-N-(6-hydroxyhexyl)-3-cyclohexyl-N$^\alpha$-methyl-L-alaninamide monohydrochloride The title compound is prepared by the method of Example 16 using the title product of Example 67.

EXAMPLE 70 t-butoxycarbonyl-N-ethyl-L-tyrosine

To a stirred mixture of 18.6 g (50 mmole) of t-butoxycarbonyl-O-benzyl-L-tyrosine in 400 ml of freshly dried tetrahydrofuran cooled to $-78°$ was added dropwise 58 ml of 1.9 M t-butyl lithium in pentane. After warming to $-20°$, the solution was stirred for 1.5 hours, and 9.5 g (50 mmole) of triethyloxonium fluoborate was then added. After about one hour the mixture was poured into and shaken with aqueous sodium bisulfate (giving a pH of 3 in the aqueous phase). The aqueous phase was washed with water, dried over sodium sulfate, filtered, and concentrated in vacuo to an oil. Purification by column chromatography on silica gel afforded 12.6 g of the O-benzyl ether derivative of the title compound as a white solid. [Analysis. Calcd. for $C_{23}H_{29}NO_5$: C, 69.15; H, 7.32; N, 3.51. Found: C, 68.70; H, 7.22; N, 3.53.]A portion (1.0 g, 2.25 mmole) of the benzyl ether intermediate in 35 ml of tetrahydrofuran was hydrogenated at room temperature using hydrogen gas at atmospheric pressure and 5% palladium on carbon as catalyst. After filtration the filtrate was concentrated to dryness and purified by column chromatography, giving the analytically pure title compound.

$[\alpha]_D$ $-124.4°$; $[\alpha]_{365}$ $-447.8°$ (chloroform)
Analysis. Calcd. for $C_{16}H_{23}NO_5$:
C, 62.12; H, 7.49; N, 4.53.
Found: C, 62.14; H, 7.81; N, 4.73.

EXAMPLE 71 t-butoxycarbonyl-N$^\alpha$-ethyl-O-(2-methylpropoxycarbonyl)-L-tyrosyl-D-methionylglycyl-N-(6-methoxy-6-oxohexyl)-L-phenylalaninamide The title compound was prepared from 2.09 g (6.8 mmole) of the title product of Example 70, using the general method described in Example 13 (and Example 1) except that a two-fold quantity (1.77 ml, ca. 13.5 mmole) of isobutylchloroformate was employed. Purification by column chromatography on silica gel afforded 3.75 g of the title compound as an analytically pure glassy solid.
Analysis. Calcd. for $C_{44}H_{65}N_5O_{11}S$:
C, 60.60; H, 7.51; N, 8.03; S, 3.68.
Found: C, 60.55; H, 7.55; N, 8.02; S, 3.68.

Example 72

N$^\alpha$-ethyl-O-(2-methylpropoxycarbonyl-L-tyrosyl-D-methionylglycyl-N-(6-methoxy-6-oxohexyl)-L-phenylalaninamide monohydrochloride (SC-36763)

The title compound was prepared by the method of Example 14 using 1.7 g (1.9 mmole) of the title product of Example 71. Structure assignment was supported by elemental analysis. $[\alpha]_D$ $+36.0$; $[\alpha]_{365}$ $+132.0$ (methanol)
Analysis. Calcd. for $C_{39}H_{57}N_5O_9S$·HCl:
C, 57.94; H, 7.23; N, 8.66; S, 3.97; Cl, 4.38.
Found: C, 57.79; H, 7.13; N, 8.77; S, 4.06; Cl, 4.46.

EXAMPLE 73

N$^\alpha$-ethyl-O-(2-methylpropoxycarbonyl)-L-tyrosyl-[4-(methylsulfinyl)-D-2-aminobutanoyl]glycyl-N-(6-methoxy-6-oxohexyl)-L-phenylalaninamide monohydrochloride (SC-36792)

The title compound was prepared by the method of Example 16 using the title product of Example 72. Structure assignment was supported by elemental analysis.
Analysis. Calcd. for $C_{39}H_{57}N_5O_{10}S$·HCl:
C, 56.82; H, 7.09; N, 8.50; S, 3.89; Cl, 4.30.
Found: C, 56.88; H, 6.98; N, 8.48; S, 3.99; Cl, 4.40.

EXAMPLE 74 t-butoxycarbonyl-N$^\alpha$-ethyl-L-tyrosyl-D-methionylglycyl-N-(6-methoxy-6-oxohexyl)-L-phenylalaninamide monohydrochloride hemihydrate (SC-36821)

To a stirred mixture of 1.7 g (1.9 mmole) of the title product of Example 71 in 40 ml of methanol was added 10 ml of 10% aqueous potassium carbonate. After about 75 minutes the resultant solution was poured into a mixture of 150 ml of dichloromethane and 100 ml of 0.5 M potassium bisulfate. The organic phase (containing the crude neutralized product) was separated and the aqueous layer was further extracted with dichloromethane. The combined organic layers were concentrated to dryness and purified by column chromatography, giving the analytically pure BOC-protected derivative of the title compound. [Analysis. Calcd. for $C_{39}H_{57}N_5O_9S$: C, 60.68; H, 7.44; N, 9.07; S, 4.15. Found: C, 60.64; H, 7.52; N, 8.90; S, 4.01.] The intermediate thus formed was converted to the title compound by the method described in Example 14. Structure Assignment was supported by elemental analysis.
Analysis. Calcd. for $C_{34}H_{49}N_5O_7S$·HCl·½H$_2$O:
C, 56.93; H, 7.17; N, 9.77; S, 4.47; Cl, 4.94.
Found: C, 56.98; H, 7.05; N, 9.82; S, 4.35; Cl, 5.11.

Example 75

N$^\alpha$-ethyl-L-tyrosyl-[4-(methylsulfinyl)-D-2-aminobutanoyl]glycyl-N-(6-methoxy-6-oxohexyl)-L-phenylalaninamide monohydrochloride hemihydrate (SC-36825)

The title compound was prepared by the method of Example 16 using the title product of Example 74. Structure assignment was supported by elemental analysis.
Analysis. Calcd. for $C_{34}H_{49}N_5O_8S$·HCl·H$_2$O:
C, 55.68; H, 7.01; N, 9.55; S, 4.37; Cl, 4.83.
Found: C, 55.44; H, 6.87; N, 9.47; S, 4.23; Cl, 4.99.

Example 76

O-(2-methylpropoxycarbonyl)-2,3,6-trimethyltyrosyl-D-methionylglycyl-N-(6-methoxy-6-oxohexyl)-L-phenylalaninamide monohydrochloride trihydrate (SC-36874)

Using t-butoxycarbonyl-2,3,6-trimethyltyrosine prepared from 2,3,5-trimethylphenol by the method of Example 12, the title compound was prepared by the methods of Examples 71 (basically the method of Example 13 without resolution of the racemic mixture) and 14. Structure assignment was supported by elemental analysis.

Analysis. Calcd. for $C_{40}H_{59}N_5O_9S \cdot HCl \cdot 3H_2O$:
C, 54.81; H, 7.58; N, 7.99; S, 3.66; Cl, 4.04.
Found: C, 54.87; H, 6.93; N, 8.07; S, 3.81; Cl, 4.12.

EXAMPLE 77

O-(2-methylpropoxycarbonyl)-2,3,6-trimethyltyrosyl-[4-(methylsulfinyl)-D-2-aminobutanoyl]glycyl-N-(6-methoxy-6-oxohexyl)-L-phenylalaninamide monohydrochloride sesquihydrate (SC-36889)

The title compound was prepared by the method of Example 16 using the title product of example 76. Structure assignment was supported by elemental analysis.

Analysis. Calcd. for $C_{40}H_{59}N_5O_{10}S \cdot HCl \cdot 3/2H_2O$:
C, 56.02; H, 7.40; N, 8.17; S, 3.74; Cl, 4.13.
Found: C, 56.18; H, 7.14; N, 8.23; S, 3.80; Cl, 4.11.

EXAMPLE 78

2,3,6-trimethyl-L-tyrosyl-D-methionylglycyl-N-(6-methoxy-6-oxohexyl)-L-phenylalaninamide monohydrochloride hemihydrate (SC-37279)

Using t-butoxycarbonyl-2,3,6-trimethyltyrosine prepared from 2,3,5-trimethylphenol by the method of Example 12, the title compound was prepared by the methods of Examples 71 (except that the racemic mixture was separated as in Example 13) and 74. Structure assignment was supported by elemental analysis. $[\alpha]_D +23.3°$; $[\alpha]_{365} +100.0°$ (methanol)

Analysis. Calcd. for $C_{35}H_{51}N_5O_7S \cdot HCl \cdot \frac{1}{2}H_2O$: C, 57.48; H, 7.30; N, 9.58; S, 4.38; Cl, 4.85. Found: C, 57.13; H, 7.01; N, 9.50; S, 4.60; Cl, 5.10.

EXAMPLE 79

2,3,6-trimethyl-D-tyrosyl-D-methionylglycyl-N-(6-methoxy-6-oxohexyl)-L-phenylalaninamide monohydrochloride hemihydrate (SC-37277)

The title compound was prepared by the methods summarized in
Example 78, except for using the isomer having 2,3,6-trimethyl-D-tyrosine. Structure assignment was supported by elemental analysis.
$[\alpha]_D -49.8°$; $[\alpha]_{365} -186.5°$ (methanol)

Analysis. Calcd. for $C_{35}H_{51}N_5O_7S \cdot HCl \cdot \frac{1}{2}H_2O$:
C, 57.48; H, 7.30; N, 9.58; S, 4.38; Cl, 4.85.
Found C, 57.13; H, 6.99; N, 9.49; S, 4.49; Cl, 5.10.

EXAMPLE 80

2,3,6-trimethyl-L-tyrosyl-[4-methylsulfinyl)-D-2-aminobutanoyl]glycyl-N-(6-methoxy-6-oxohexyl)-L-phenylalaninamide monohydrochloride monohydrate (SC-37336)

The title compound was prepared by the method of Example 16 using the title product of Example 78. Structure assignment was supported by elemental analysis. $[\alpha]_D +40.4°$; $[\alpha]_{365} +150.7°$ (methanol)

Analysis. Calcd. for $C_{35}H_{51}N_5O_8S \cdot HCl \cdot H_2O$:
C, 55.58; H, 7.19; N, 9.26; S, 4.23; Cl, 4.69.
Found: C, 55.60; H, 7.01; N, 9.26; S, 4.23; Cl, 4.86.

EXAMPLE 81

2,3,6-trimethyl-D-tyrosyl-[4-methylsulfinyl)-D-2-aminobutanoyl]glycyl-N-(6-methoxy-6-oxohexyl)-L-phenylalaninamide monohydrochloride monohydrate (SC-37334)

The title compound was prepared by the method of Example 16 using the title product of Example 79. Structure assignment was supported by elemental analysis. $[\alpha]_D -46.2°$; $[\alpha]_{365} -166.2°$ (methanol)

Analysis. Calcd. for $C_{35}H_{51}N_5O_8S \cdot HCl \cdot H_2O$:
C, 55.58; H, 7.19; N, 9.26; S, 4.23; Cl, 4.69.
Found: C, 55.98; H, 7.01; N, 9.19; S, 4.23; Cl, 5.14.

EXAMPLE 82

O-(2-methylpropoxycarbonyl)-2-methyltyrosyl-D-methionylglycyl-N-(6-methoxy-6-oxohexyl)-L-phenylalaninamide monohydrochloride hemihydrate (SC-36886)

Using t-butoxycarbonyl-2-methyltyrosine prepared from 3-methylphenol by the method of Example 12, the title compound was prepared by the methods of Examples 71 (basically the method of Example 13 without resolution of the racemic mixture) and 14. Structure assignment was supported by elemental analysis.

Analysis. Calcd. for $C_{38}H_{55}N_5O_9S \cdot HCl \cdot \frac{1}{2}H_2O$:
C, 56.80; H, 7.15; N, 8.71; S, 3.99; Cl, 4.41.
Found: C, 56.80; H, 7.05; N, 8.82; S, 4.09; Cl, 4.47.

EXAMPLE 83

O-(2-methythylpropoxycarbonyl)-2-methyltyrosyl-[4-(methylsulfinyl)-D-2-aminobutanoyl]-glycyl-N-(6-methoxy-6-oxohexyl)-L-phenylalaninamide monohydrochloride hemihydrate (SC-36899)

The title compound was prepared by the method of Example 16 using the title product of Example 82. Structure assignment was supported by elemental analysis.

Analysis. Calcd. for $C_{38}H_{55}N_5O_{10}S \cdot HCl \cdot H_2O$:
C, 55.69; H, 7.01; N, 8.55; S, 3.91; Cl, 4.33.
Found C, 55.53; H, 7.00; N, 8.73; S, 3.90; Cl, 4.39.

EXAMPLE 84

2-methyl-L-tyrosyl-D-methionylglycyl-N-(6-methoxy-6-oxohexyl -L-phenylalaninamide monohydrochloride Using t-butoxycarbonyl-2-methyltyrosine prepared from 3-methylphenol by the method of Example 12, the title compound is prepared by the methods of Examples 71 (except that the racemic mixture is separated as in Example 13) and 71.

EXAMPLE 85

2-methyl-D-tyrosyl-D-methionylglycyl-N-(6-methoxy-6-oxohexyl)-L-phenylalaninamide monohydrochloride The title compound is prepared by the methods summarized in Example 84, except for using the isomer having 2-methyl-D-tyrosine.

EXAMPLE 86

2-methyl-L-tyrosyl-[4-(methylsulfinyl)-D-2-aminobutanoyl]glycyl-N-(6-methoxy-6-oxohexyl)-L-phenylalaninamide monohydrochloride The title compound is prepared by the method of Example 16 using the title product of Example 84.

EXAMPLE 87

2-methyl-D-tyrosyl-[4-(methylsulfinyl)-D-2-aminobutanoyl]glycyl-N-(6-methoxy-6-oxohexyl)-L-phenylalaninamide monohydrochloride The title compound is prepared by the method of Example 16 using the title product of Example 85.

EXAMPLE 88

O-(2-methylpropoxycarbonyl)-3-t-butyl tyrosyl-D-methionylglycyl-N-(6-methoxy-6-oxohexyl)-L-phenylalaninamide monohydrochloride (SC-36898)

Using t-butoxycarbonyl-3-t-butyltyrosine prepared from 2-t-butylphenol by the method of Example 12, the title compound was prepared by the methods of Examples 71 (basically the method of Example 13 without resolution of the racemic mixture) and 14. Structure assignment was supported by elemental analysis.
Analysis. Calcd. for $C_{41}H_{61}N_5O_9S \cdot HCl$:
C, 58.87; H, 7.47; N, 8.37; S, 3.83; Cl, 4.24.
Found: C, 58.53; H, 7.52; N, 8.35; S, 3.79; Cl, 4.24.

EXAMPLE 89

O-(2-methylpropoxycarbonyl)-3-t-butyltyrosyl-[4-(methylsulfinyl)-D-2-aminobutanoyl]glycyl-N-(6-methoxy-6-oxohexyl)-L-phenylalaninamide monohydrochloride hemihydrate (SC-36933)

The title compound was prepared by the method of Example 16 using the title product of Example 88. Structure assignment was supported by elemental analysis.
Analysis. Calcd. for $C_{41}H_{61}N_5O_{10}S \cdot HCl \cdot \frac{1}{2}H_2O$:
C, 57.16; H, 7.37; N, 8.13; S, 3.72; Cl, 4.11.
Found: C, 57.12; H, 7.36; N, 8.13; S, 3.68; Cl, 3.98.

EXAMPLE 90

3-t-butyl-L-tyrosyl-D-methionylglycyl-N-(6-methoxy-6-oxohexyl)-L-phenylalaninamide monohydrochloride (SC-39926)

Using t-butoxycarbonyl-3-t-butyltyrosine prepared from 2-t-butylphenol by the method of Example 12, the title compound was prepared by the methods of Examples 71 (except that the racemic mixture was separated as in Example 13) and 74. Structure assignment was supported by elemental analysis.
$[\alpha]_D \pm 6.8°$; $[\alpha]_{365} +27.5°$ (methanol)
Analysis. Calcd. for $C_{36}H_{53}N_5O_7S \cdot HCl$:
C, 58.72; H, 7.39; N, 9.51.
Found: C, 58.58; H, 7.39; N, 9.30.

EXAMPLE 91

3-t-butyl-D-tyrosyl-D-methionylglycyl-N-(6-methoxy-6-oxohexyl)-L-phenylalaninamide monohydrochloride (SC-39913)

The title compound was prepared by the methods summarized in Example 90, except for using the isomer having 3-t-butyl-D-tyrosine. Structure assignment was supported by elemental analysis.
$[\alpha]_D -19.4°$; $[\alpha]_{365} -92.3°$ (methanol)
Analysis. Calcd. for $C_{36}H_{53}N_5O_7S \cdot HCl$:
C, 58.72; H, 7.39; N, 9.51; S, 4.35.
Found: C, 58.47; H, 7.42; N, 9.52; S, 4.35.

EXAMPLE 92

3-t-butyl-L-tyrosyl-[4-(methylsulfonyl)-D-2-aminobutanoyl]glycyl-N-(6-methoxy-6-oxohexyl)-L-phenylalaninamide monohydrochloride hemihydrate (SC-39983)

The title sulfone was prepared from the title product of Example 90 using the method of Example 16, except that the methanolic hydrogen peroxide solution was heated at reflux for about one hour. Structure assignment was supported by elemental analysis.
$[\alpha]_D +14.2°$; $[\alpha]_{365} +60.4°$ (methanol)
Analysis. Calcd. for $C_{36}H_{53}N_5O_9S \cdot HCl \cdot \frac{1}{2}H_2O$:
C, 55.62; H, 7.13; N, 9.01.
Found: C, 55.38; H, 7.29; N, 9.03.

EXAMPLE 93

3-t-butyl-D-tyrosyl-[4-(methylsulfonyl)-D-2-aminobutanoyl]glycyl-N-(6-methoxy-6-oxohexyl)-L-phenylalaninamide monohydrochloride hemihydrate (SC-39967)

The title compound was prepared by the method of Example 92 using the title product of example 91. Structure assignment was supported by elemental analysis.
$[\alpha]_D -16.0°$; $[\alpha]_{365} -64.9°$ (methanol)
Analysis. Calcd. for $C_{36}H_{53}N_5O_9S \cdot HCl \cdot 178 H_2O$:
C, 55.62; H, 7.13; N, 9.01.
Found: C, 55.20; H, 7.21; N, 9.00.

EXAMPLE 94

2,4-dimethyl-3-(2-methylpropoxycarbonyloxy)-phenylalanyl-D-methionylglycyl-N-(6-methoxy-6-oxohexyl)-L-phenylalaninamide monohydrochloride chloride hemihydrate (SC-36888)

Using t-butoxycarbonyl-2,4-dimethyl-3-hydroxyphenylalanine prepared from 2,6-dimethylphenol by the method of Example 12, the title compound was prepared by the methods of Examples 71 (basically the method of Example 13 without the resolution of the racemic mixture) and 14. Structure assignment was supported by elemental analysis.
Analysis. Calcd. for $C_{39}H_{57}N_5O_9S \cdot HCl \cdot \frac{1}{2}H_2O$:
C, 57.30; H, 7.27; N, 8.57; S, 3.92; Cl, 4.34.
Found: C, 57.30; H, 7.18; N, 8.57; S, 3.96; Cl, 4.30.

EXAMPLE 95

2,4-dimethyl-3-(2-methylpropoxycarbonyloxy)-phenylalanyl-[4-(methylsulfinyl)-D-2-aminobutanoyl]glycyl-N-(6-methoxy-6-oxohexyl)-L-phenylalaninamide monohydrochloride hemihydrate (SC-36917)

The title compound was prepared by the method of Example 16 using the title product of example 94. Structure assignment was supported by elemental analysis.
Analysis. Calcd. for $C_{39}H_{57}N_5O_{10}S \cdot HCl \cdot 2H_2O$:
C, 54.44; H, 7.26; N, 8.14; S, 3.73; Cl, 4.12.
Found: C, 54.38; H, 6.77; N, 8.14; S, 3.78; Cl, 4.12.

EXAMPLE 96

2,4-dimethyl-3-hydroxyphenylalanyl-D-methionyl-glycyl-N-(6-methoxy-6-oxohexyl)-L-phenylalanamide monohydrochloride hemihydrate (SC-40367)

Using t-butoxycarbonyl-2,4-dimethyl-3-hydroxyphenylalanine prepared from 2,6-dimethylphenol by the method of Example 12, the title compound was prepared by the methods of Examples 71 (without the resolution of the racemic mixture) and 74. Structure assignment was supported by elemental analysis.

Analysis. Calcd. for $C_{33}H_{49}N_5O_8S.HCl.\frac{1}{2}H_2O$:
C, 54.94; H, 7.13; N, 9.71.
Found: C, 54.84; H, 6.66; N, 9.26.

EXAMPLE 97

2,6-dimethyl-L-tyrosyl-D-alanylglycyl-N-(6-methoxy-6-oxohexyl)-L-phenylalanamide monohydrochloride (SC-39865)

The title compound was prepared by the methods of Examples 8 (except for using t-butoxycarbonyl-D-alanine instead of t-butoxycarbonyl-D-methionine), 9, 10, 11, 13 and 14. Structure assignment was supported by elemental analysis.

$[\alpha]_D$ +53.9°; $[\alpha]_{365}$ +200° (methanol)
Analysis. Calcd. for $C_{32}H_{45}N_5O_7.HCl$:
C, 59.20; H, 7.30; N, 10.79.
Found: C, 58.83; H, 7.14; N, 10.53.

EXAMPLE 98

2,6-dimethyl-D-tyrosyl-D-alanylglycyl-N-(6-methoxy-6-oxohexyl)-L-phenylalanamide monohydrochloride hemihydrate (SC-39804)

The title compound was prepared by the methods summarized in Example 97, except for using the method of Example 15 instead of Example 14. Structure assignment was supported by elemental analysis.

$[\alpha]_D$ −33 3°; $[\alpha]_{365}$ −122.2° (methanol)
Analysis Calcd. for $C_{32}H_{45}N_5O_7.HCl.\frac{1}{2}H_2O$:
C, 58.48; H, 7.21; N, 10.66.
Found: C, 58.45; H, 7.18; N, 10.56.

EXAMPLE 99A t-butoxycarbonyl-D-norleucylglycine, methyl ester

The title compound was prepared by the general method of Example 1 using 15.0 g (65 mmol) of t-butoxycarbonyl-D-norleucine (Boc-D-Nle) and 8.1 g (65 mmol) of glycine methyl ester hydrochloride. Trituration of the product oil with diethyl ether and (Skellysolve B) produced 18.2 g of the title compound as a pale yellow solid. Structure assignment was supported by elemental analysis.

Analysis. Calcd. for $C_{14}H_{26}N_2O_5$: C, 55.61; H, 8.67; N, 9.27. Found: C, 55.31; H, 8.72; N, 9.22.

EXAMPLE 99 t-butoxycarbonyl-D-norleucylglycine

The title compound was prepared by the general method of Example 9 using the title product of Example 99A in place of the title product of Example 8. Structure assignment was supported by elemental analysis.

Analysis Calcd. for $C_{13}H_{24}NO_5$: C, 54.15; H, 8.39; N, 9.72. Found: C, 53.83; H, 8.47; N, 9.42.

EXAMPLE 100 t-butoxycarbonyl-D-norleucylglycyl-3-cyclohexyl-N-(6-methoxy-6-oxohexyl)-L-alaninamide After preparing N-(6-methoxy-6-oxohexyl)-3-cyclohexyl-L-alaninamide monohydrochloride from the title product of Example 36 by the methods of Examples 1 and 3, the title compound was prepared by coupling this material with the title product of Example 99 using the general mixed anhydride procedure of Example 1. Structure assignment of the product isolated by chromotography was supported by elemental analysis.

Analysis. Calcd. for $C_{13}H_{24}NO_5$: C, 61.24; H, 9.22; N, 9.85. Found: C, 61.13; H, 9.19; N, 9.79.

EXAMPLE 101

D-norleucylglycyl-3-cyclohexyl-N-(6-methoxy-6-oxohexyl)-L-alaninamide, monohydrochloride The title compound was prepared by the method of Example 11 using the title compound of Example 100. Structure assignment was supported by elemental analysis.

Analysis. Calcd. for $C_{24}H_{45}N_4O_5Cl.\frac{1}{2}H_2O$: C, 56.06; H, 9.02; N, 10.90. Found: C, 56.37; H, 9.07; N, 11.08.

EXAMPLE 102 t-butoxycarbonyl-0-[(2-methylpropoxy)carbonyl]-2,6-dimethyl-D,L-tyrosyl-D-norleucylglycyl-6-cyclohexyl-N-(6-methoxy-6-oxohexyl)-L-alaninamide The title compounds, a mixture of the D,L diastereomers, were prepared from the title compounds of Example 12 and Example 101 using the general mixed anhydride procedure described in Example 71 (and Examples 13 and 1). The title compounds were isolated by column chromatography and structure assignments were supported by elemental analysis.

Analysis. Calcd. for $C_{45}H_{73}N_5O_{11}$: C, 62.84; H, 8.55; N, 8.14. Found: C, 62.76; H, 8.42; N, 8.29.

EXAMPLE 103 t-butoxycarbonyl-2,6-dimethy-D,L-tyrosyl-D-norleucylglycyl-3-cyclohexyl-N-(6-methoxy-6-oxohexyl)-L-alaninamide The title compounds, a mixture of fast moving diastereomer (D) and slow moving diastereomer (L) (as determined by TLC in 5% EtOH/CHCl₃) were prepared by the method of Example 74 using the title product of Example 102. The title diastereomers were separated by column chromatography on silica gel and structure assignments were supported by elemental analysis.

Diastereomer D: $[\alpha]_D$−41.7° (CHCl₃)
Analysis. Calcd. for $C_{40}H_{65}N_5O_9$: C, 63.22; H, 8.62; N, 9.22. Found: C, 62.96; H, 8.55; N, 9.12.
Diastereomer L: $[\alpha]_D$+5.0 (CHCl₃)
Analysis. Calcd. for $C_{40}H_{65}N_5O_9$: C, 63.22; H, 8.62; N, 9.22. Found: C, 63.29; H, 8.69; N, 9.16.

EXAMPLE 104

2,6-dimethyltyrosyl-D-norleucylglycyl-3-cyclohexyl-N-(6-methoxy-6-oxohexyl)-L-alaninamide, monohydrochloride(diastereomer-D)

The title compound was prepared by the method of Example 14 using diastereomer-D of Example 103.

Structure assignement was supported by elemental analysis.

$[\alpha]_D$ −56.0 (MeOH)

Analysis. Calcd. for $C_{35}H_{58}N_5O_7Cl.H_2O$: C, 58.84; H, 8.46; N, 9.80. Found: C, 59.09; H, 8.14; N, 10.11.

EXAMPLE 105

2,6-dimethyltyrosyl-D-norleucylglycyl-3-cyclohexyl-N-(6-methoxy-6-oxohexyl)-L-alaninamide, monohydrochloride(diastereomer-L)

The title compound was prepared by the method of Example 14 using the L-diastereomer of Example 103. Structure assignment was supported by elemental analysis. $[\alpha]_D$ +23.0 (MeOH)

Analysis. Calcd. for $C_{35}H_{58}N_5O_7Cl.\frac{1}{2}H_2O$: C, 59.60; H, 8.43; N, 9.93. Found: C, 59.49; H, 8.21; N, 9.98.

EXAMPLE 106 t-butoxycarbonyl-D-norleucylglycyl-3-cyclohexyl-N-(6-methoxy-6-oxohexyl)-N$^\alpha$-methy 1-L-alaninamide After preparing N-(6-methoxy-6-oxohexyl)-3-cyclohexyl-N$^\alpha$-methyl-L-alaninamide monohydrochloride from the title product of Example 42 by the methods of Example 1 and 3, the title compound is prepared by coupling this material with the title product of Example 99 using the general mixed anhydride procedure of Example 1.

EXAMPLE 107

D-norleucylglycyl-3-cyclohexyl-N-(6-methoxy-6-oxohexyl)-N$^\alpha$-methyl-L-alaninamide, monohydrochloride The title compound is prepared by the method of Example 11 using the title compound of Example 106.

EXAMPLE 108 t-butoxycarbonyl-O-[(2-methylpropoxy)carbonyl]-2,6-dimethyl-D,L-tyrosyl-D-norleucylglycyl-3-cyclohexyl-N-(6-methoxy-6-oxohexyl)-N$^\alpha$-methyl-L-alaninamide The title compounds, a mixture of two diastereomers, are prepared from the title compounds of Example 12 and Example 107 using the general mixed anhydride procedure described in Example 71 (and Examples 13 and 1).

EXAMPLE 109 t-butoxycarbonyl-2,6-dimethyl-D,L-tyrosyl-D-norleucylglycyl-3-cyclohexyl-N-(6-methoxy-6-oxohexyl)-N$^\alpha$-methyl-L-alaninamide The title compounds, a mixture of fast moving diastereomer (D) and slow moving diasteromer (L) (as determined by TLC in 5% EtOH/CHCl$_3$), are prepared by the method of Example 74 using the title product of Example 108. The title diastereomers are separated by column chromatography on silica gel as described previously.

EXAMPLE 110

2,6-dimethyltyrosyl-D-norleucylglycyl-3-cyclohexyl-N-(6-methoxy-6-oxohexyl)-N$^\alpha$-methy 1-L-alaninamide, monohydrochloride (diastereomer-D)

The title compound is prepared by the method of Example 14 using the D-diastereomer of Example 109.

EXAMPLE 111

2,6-dimethyltyrosyl-D-norleucylglycyl-3-cyclohexyl-N-(6-methoxy-6-oxohexyl)-N$^\alpha$-methyl-L-alaninamide, monohydrochloride (diastereomer-L)

The title compound is prepared by the method of Example 14 using the L-diastereomer of Example 109.

EXAMPLE 112 t-butoxycarbonylglycyl-3-cyclohexyl-N-(6-methoxy-6-oxohexyl)-N$^\alpha$-methyl-L-alaninamide After preparing N-(6-methoxy-6-oxohexyl)13-cyclohexyl-N$^\alpha$-methyl-L-alaninamide monohydrochloride from the title product of Example 42 by the methods of Examples 1 and 3, 21.8 g (62.5 mmol) were coupled with 10.9 g (62.5 mmol) of Boc-Gly by the method of Example 1. The title compound (21.7 g) was obtained by silica gel chromatography of the crude reaction mixture. The product oil was used without further purification and the structure was supported by the nmr spectrum.

EXAMPLE 113 glycyl-3-cyclohexyl-N-(6-methoxy-6-oxohexyl)-N$^\alpha$-methyl-L-alaninamide, monohydrochloride The title compound was prepared by the method of Example 3. Structure assignment was supported by elemental analysis.

$[\alpha]_D$ −37.6 (MeOH)

Analysis. Calcd. for $C_{19}H_{36}N_3O_4Cl$: C, 55.59; H, 8.84; N, 10.24; Cl, 8.64. Found: C, 55.43; H, 8.47; N, 10.11; Cl, 8.89.

EXAMPLE 114 t-butoxycarbonyl-2,6-dimethyl-D,L-tyrosyl-D-alanine, methyl ester

The title mixture of diastereomers was prepared by the method of Example 1 using (d)Ala-OMe and the title compound of Example 12. The crude products were used without purification.

EXAMPLE 115 t-butoxycarbonyl-2,6-dimethyl-D,L-tyrosyl-D-alanine

The title compounds of Example 114 were saponified by the method of Example 9. The mixture of diastereomers was separated by silica gel chromatography to give by TLC (Example 103) a fast (D) isomer and a slow (L) isomer.

Diastereomer D: $[\alpha]_D$ −21.7(CHCl$_3$)

Analysis. Calcd. for $C_{19}H_{28}N_2O_6$: C, 59.99; H, 7.42; N, 7.36. Found: C, 59.31; H, 7.42; N, 7.01.

Diastereomer L: $[\alpha]_D$ +16.5(CHCl$_3$)

Analysis. Calcd. for $C_{19}H_{28}N_2O_5$: C, 58,88; H, 7.42; N, 7.36. Found: C, 59.19; H, 7.44; N, 7.17.

EXAMPLE 116 t-butoxycarbonyl-2,6-dimethyltyrosyl D-alanylglycyl-3-cyclohexyl-N-(6-methoxy-6-oxohexyl)-N$^\alpha$-methyl-L-alaninamide, (diastereomer-D)

The title compound is prepared by the method of Example 1 from the title product of Example 113 and the fast diastereomer (D) of Example 114.

EXAMPLE 117

2,6-dimethyltyrosyl-D-alanylglycyl-3-cyclohexyl-N-(6-methoxy-6-oxohexyl)-N$^\alpha$-methyl-L-alaninamide, monohydrochloride (diastereomer-D)

The title compound is prepared from the title product of Example 116 using the method of Example 3.

EXAMPLE 118

2,6-dimethyltyrosyl-D-alanylglycyl-3-cyclohexyl-N-(6-methoxy-6-oxohexyl)-N$^\alpha$-methyl-L-alaninamide, monohydrochloride (diastereomer-L)

The title compound is prepared by the mixed anhydride coupling method of Example 1 from the title product of Example 113 and the slow diastereomer (L) of Example 114.

EXAMPLE 119

2,6-dimethyltyrosyl-D-alanylglycyl-3-cyclohexyl-N-(6-methoxy-6-oxohexyl)-N$^\alpha$-methyl-L-alaninamide, monohydrochloride (diastereomer-L)

The title compound is prepared from the title product of Example 118 using the methods of Example 3.

EXAMPLE 120 t-butoxycarbonylglycyl-3-cyclohexyl-N-(6-methoxy-6-oxohexyl)-L-alaninamide

After preparing N-(6-methoxy-6-oxohexyl)-3-cyclohexyl-L-alaninamide monohydrochloride from the title product of Example 36 by the methods of Example 1 and 3, it is coupled with Boc-Gly by the methods of Example 1.

EXAMPLE 121 glycyl-3-cyclohexyl-N-(6-methoxy-6-oxohexyl)-L-alaninamide, monohydrochloride

The title compound is prepared by the method of Example 3.

EXAMPLE 122 t-butoxycarbonyl-2,6-dimethyltyrosyl-D-alanylglycyl-3-cyclohexyl-N-(6-methoxy-6-oxohexyl)-L-alaninamide, (diastereomer-D)

The title compound is prepared by the method of Example 1 from the title product of Example 121 and the fast diastereomer (D) of Example 114.

EXAMPLE 123

2,6-dimethyltyrosyl-D-alanylglycyl-3-cyclohexyl-N-(6-methoxy-6-oxohexyl)-L-alaninamide, monohydrochloride, diastereomer-(D)

The title compound is prepared from the title product of Example 122 using the method of Example 3.

EXAMPLE 124

2,6-dimethyltyrosyl-D-alanylglycyl-3-cyclohexyl-N-(6-methoxy-6-oxohexyl)-L-alaninamide, monohydrochloride, diastereomer-(L)

The title compound is prepared by the method of Example 1 from the title product of Example 121 and the slow diastereomer (L) of Example 114.

EXAMPLE 125

2,6-dimethyltyrosyl-D-alanylglycyl-3-cyclohexyl-N-(6-methoxy-6-oxohexyl)-L-alaninamide, monohydrochloride, diastereomer-(L)

The title compound is prepared by the method of Example 1 from the title product of Example 124.

EXAMPLE 126 t-butoxycarbonyl-2,6-dimethyl-L-tyrosyl-D-methionylglycyl-N-(5-carboxypentyl)-3-cyclohexyl-L-alaninamide, monohydrochloride The Boc protected precursor of the title compound of Example 37, the preparation of which is described in Example 37, was soponified by the methods described in Example 9 to generate the title material.
$[\alpha]_D$ −0.5° (McOH)

Analysis Calcd. for $C_{38}H_{61}N_5O_9S$: C, 59.74; H, 8.05; N, 9.17; S, 4.20. Found: C, 59.70; H, 8.32; N, 8.63; S, 3.83.

EXAMPLE 127

2,6-dimethyl-L-tyrosyl-D-methionylglycyl-N-(5-carboxypentyl)-3-cyclohexyl-L-alaninamide, monohydrochloride The title compound was prepared by the method of Example 14 from the title product of Example 126.
$[\alpha]_D$ +48.8 (MeOH)

Analysis Calcd. for $C_{33}H_{53}N_5O_7S \cdot Hcl$: C, 56.60; H, 7.77; N, 10.00; S, 4.58; Cl, 5.06. Found: C, 57.08; H, 7.72; N, 9.74; S, 4.37; Cl, 5.10.

EXAMPLE 128

Analgesic Activity

The compounds of the invention were evaluated with respect to analgesic activity utilizing the test procedures described previously. Set forth in Table I below are the test results in the writhing assay for certain preferred compounds of the invention within formula I. The data summarized represents the ED$_{50}$ calculated on the basis of the number of animals protected at a dose of 10 mg/Kg of the active test compound compared to saline controls.

TABLE I

| Compound Example No. | Activity (ED$_{50}$ mg/Kg - Administered Subcutaneously) |
| --- | --- |
| 37 | 0.02 |
| 39 | 0.05 |
| 40 | 2.60 |
| 43 | 0.20 |
| 52 | 0.40 |
| 60 | 0.08 |
| 61 | 1.00 |
| 104 | 0.20 |
| 127 | 0.09 |

CHART A

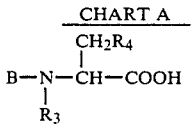

XI

"activation"

CHART A

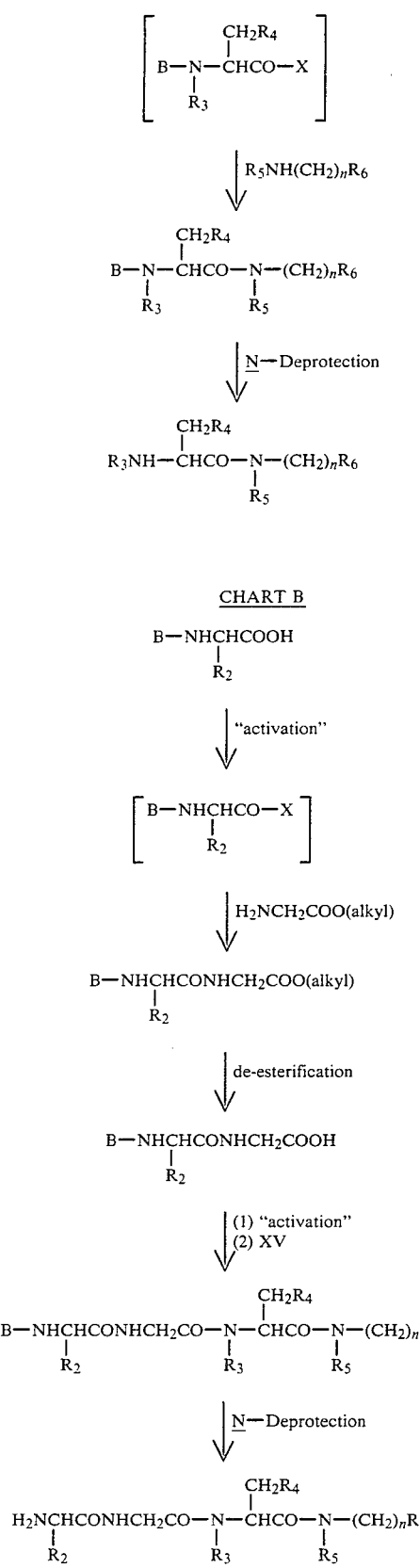

CHART B

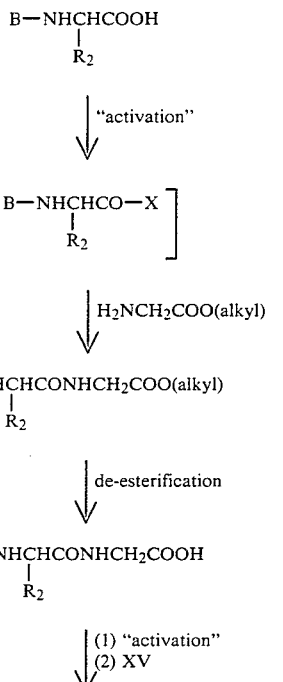

CHART C

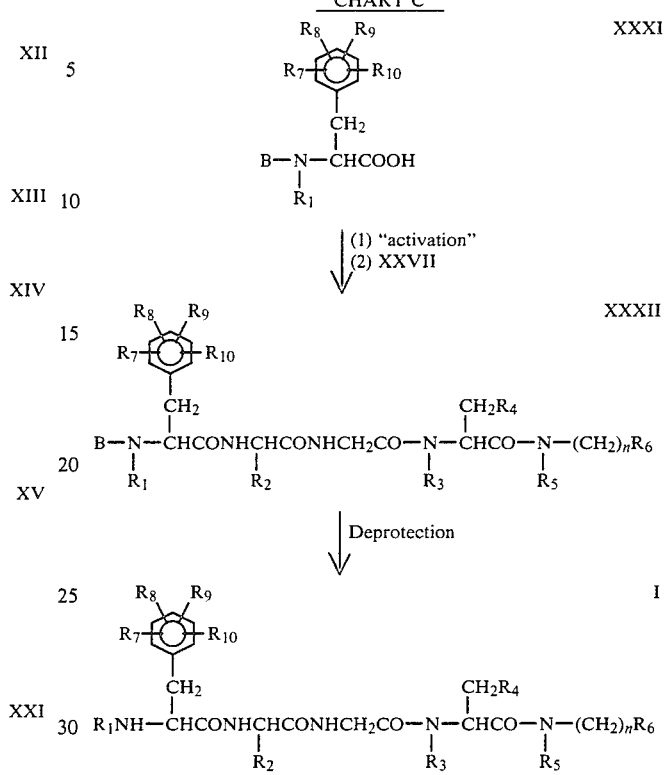

CHART D

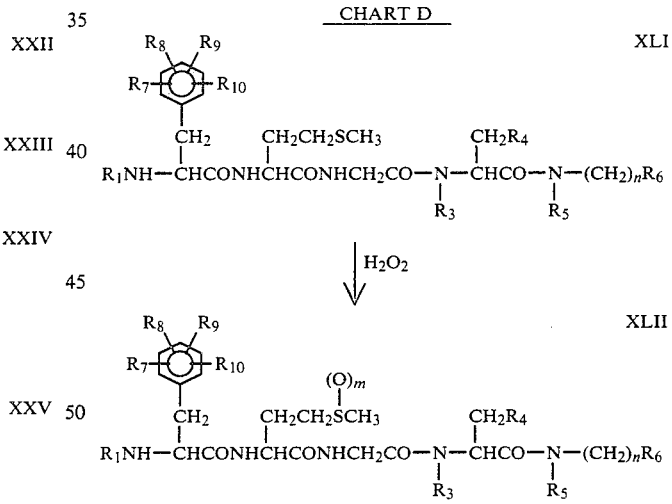

What is claimed is:

1. A compound selected from 6-dimethyl-(D,L)-tyrosyl-D-norleucylglycyl-3-cyclohexyl-N-(6-methoxy-6-oxohexyl)-L-alaninamide, 2,6-dimethyl-(D,L)-tyrosyl-D-norleucylglycyl-3-cyclohexyl-N-(6-methoxy-6-oxohexyl)-N$^\alpha$-methyl-L-alaninamide, 2,6-dimethyl-(D,L)-tyrosyl-D-alanylglycyl-3-cyclohexyl-N-(6-methoxy-6-oxohexyl)-L-alaninamide, 2,6-dimethyl-(D,L)-tyrosyl-D-alanylglycyl-3-cyclohexyl-N-(6-methoxy-6-oxohexyl)-N$^\alpha$-methyl-L-alaninamide, 2,6-dimethyl-(D,L)-tyrosyl-D-methionylglycyl-N-(5-carboxypentyl)-3-cyclohexyl-L-alaninamide, the individual tyrosyl diastereomers thereof, and the pharmacolog- 2. A compound according to claim 1 comprising 2,6-dimethyl-D-tyrosyl-D-norleucylglycyl-3-cyclohexyl-N-(6-methoxy-6-oxohexyl)-L-alaninamide and the pharmacologically acceptable acid addition salts and hydrated forms thereof.

3. A compound according to claim 1 comprising 2,6-dimethyl-L-tyrosyl-D-norleucylglycyl-3-cyclohexyl-N-(6-methoxy-6-oxohexyl)-L-alaninamide and the pharmacologically acceptable acid addition salts and hydrated forms thereof.

4. A compound according to claim 1 comprising 2,6-dimethyl-D-tyrosyl-D-norleucylglycyl-3-cyclohexyl-N-(6-methoxy-6-oxohexyl)-N$^\alpha$-methyl-L-alaninamide and the pharmacologically acceptable acid addition salts and hydrated forms thereof.

5. A compound according to claim 1 comprising 2,6-dimethyl-L-tyrosyl-D-norleucylglycyl-3-cyclohexyl-N-(6-methoxy-6-oxohexyl)-N$^\alpha$-methyl-L-alaninamide and the pharmacologically acceptable acid addition salts and hydrated forms thereof.

6. A compound according to claim 1 comprising 2,6-dimethyl-D-tyrosyl-D-alanylglycyl-3-cyclohexyl-N-(6-methoxy-6-oxohexyl)-N$^\alpha$-methyl-L-alaninamide and the pharmacologically acceptable acid addition salts and hydrated form thereof.

7. A compound according to claim 1 comprising 2,6-dimethyl-L-tyrosyl-D-alanylglycyl-3-cyclohexyl-N-(6-methoxy-6-oxohexyl)-N$^\alpha$-methyl-L-alaninamide and the pharmacologically acceptable acid addition salts and hydrated form thereof.

8. A compound according to claim 1 comprising 2,6-dimethyl-D-tyrosyl-D-alanylglycyl-3-cyclohexyl-N-(6-methoxy-6-oxohexyl)-L-alaninamide and the pharmacologically acceptable acid addition salts and hydrated forms thereof.

9. A compound according to claim 1 comprising 2,6-dimethyl-L-tyrosyl-D-alanylglycyl-3-cyclohexyl-N-(6-methoxy-6-oxohexyl)-L-alaninamide and the pharmacologically acceptable acid addition salts and hydrated forms thereof.

10. A compound according to claim 1 comprising 2,6-dimethyl-D-tyrosyl-D-methionylglycyl-N-(5-carboxypentyl)-3-cyclohexyl-L-alaninamide and the pharmacologically acceptable acid addition salts and hydrated from thereof.

11. A compound according to claim 1 comprising 2,6-dimethyl-L-tyrosyl-D-methionylglycyl-N-(5-carboxypentyl)-3-cyclohexyl-L-alaninamide and the pharmacologically acceptable acid addition salts and hydrated from thereof.

12. A pharmaceutical composition comprising an analgesically effective amount of at least one compound according to claim 1 or a pharmacologically acceptable acid addition salt or hydrated form thereof in combination with a pharmaceutically acceptable carrier.

13. A composition according to claim 12 wherein said compound is adapted for oral administration to an animal in need thereof.

14. A composition according to claim 12 wherein said compound is 2,6-dimethyl-D-tyrosyl-D-norleucylglycyl-3-cyclohexyl-N-(6-methoxy-6-oxohexyl)-L-alaninamide.

15. A method of promoting an analgesic response in an animal in need thereof comprising administering thereto an analgesically effective amount of at least one compound according to claim 1.

* * * * *